(12) United States Patent
Nagulapalli et al.

(10) Patent No.: US 6,599,753 B1
(45) Date of Patent: Jul. 29, 2003

(54) METHOD AND REAGENTS FOR THE QUANTIFICATION OF SOLID-PHASE REACTIONS USING FLUORINE NMR

(75) Inventors: Vasant K. Nagulapalli, Blue Bell, PA (US); Edward Orton, Lansdale, PA (US); John E. Airey, East Norriton, PA (US); Paul H. Krolikowski, Harleysville, PA (US); Joseph M. Salvino, Schwenksville, PA (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 09/339,397

(22) Filed: Jun. 23, 1999

Related U.S. Application Data

(63) Continuation-in-part of application No. PCT/US98/26512, filed on Dec. 14, 1998.
(60) Provisional application No. 60/090,563, filed on Jun. 24, 1998, and provisional application No. 60/090,558, filed on Jun. 24, 1998.

(51) Int. Cl.[7] .............................................. G01N 24/00
(52) U.S. Cl. ......................... 436/173; 436/124; 436/85
(58) Field of Search .................. 435/4, 6, 7.1; 436/501, 436/518, 173, 124, 85

(56) References Cited

U.S. PATENT DOCUMENTS 5,565,324 A   10/1996  Still et al.
6,133,409 A * 10/2000  Salvino et al. ............... 528/363
6,168,913 B1 * 1/2001  Hochlowski et al. .......... 435/4

FOREIGN PATENT DOCUMENTS

WO    WO 98/11036    3/1998

OTHER PUBLICATIONS

Hochlowski et al., Encoding of Combinatorial Chemistry Libraries by Fluorine–19 NMR, J.Comb.Chem. 1999, 1, 291–293.
Manatt , A Fluorine–19 NMR Approach for Studying Merrifield Solid–Phase Peptide Syntheses, Tetrahedron Letters, vol. 21, pp. 1397–1400.
Svensson et al., Use of 19F NMR spectroscopy to evaluate reactions in solid phase organic synthesis., Tetrahedron Letters vol. 37, No. 42, pp. 7649–7652.
Shapiro et al., 19F NMR Monitoring of a SNAr reaction on solid support. Tetrahedron Letters. 1996, vol. 37, No. 27, pp. 4671–4674.
Stones et al., A method for the quantification of rsin loading using 19F gel phase NMR spectroscopy and a new method for benzyl ether linker cleavage in solid phase chemistry, Tetrahedron Letters 39 (1998) 4875–4878.

* cited by examiner

*Primary Examiner*—Jill Warden
*Assistant Examiner*—Yelena Gakh
(74) *Attorney, Agent, or Firm*—George G. Wang

(57) ABSTRACT

This invention is directed to the use of $^{19}$F NMR spectroscopy to monitor and quantitate solid-phase reactions and fluorine-containing solid-phase reagents useful therefor.

11 Claims, 9 Drawing Sheets

US 6,599,753 B1

METHOD AND REAGENTS FOR THE QUANTIFICATION OF SOLID-PHASE REACTIONS USING FLUORINE NMR

CROSS-REFERENCE TO RELATED APPLICATIONS

This application is a continuation-in-part of International Application No. PCT/US98/26512, filed Dec. 14, 1998, U.S. application Ser. No. 60/090,563 and U.S. application Ser. No. 60/090,558, both filed Jun. 24, 1998. It is also related to the U.S. application Ser. No. 09/103,872, filed Jun. 24, 1998.

FIELD OF THE INVENTION

This invention is directed to the use of $^{19}$F NMR spectroscopy to monitor and quantitate solid-phase reactions, and fluorine-containing solid-phase reagents useful therefor.

BACKGROUND OF THE INVENTION

Solid-phase synthetic techniques, in which a reagent is immobilized on a polymeric material, which material is inert to the reagents and reaction conditions. employed, as well as being insoluble in the media used, are important synthetic tools for preparing amides and peptides as well as for effecting various functional group transformations. For solid-phase peptide synthesis, a summary of the many techniques employed may be found in J. M. Stewart and J. D. Young, *Solid-phase Peptide Synthesis*, 2nd. Ed., Pierce Chemical Co. (Chicago, Ill., 1984); J. Meienhofer, *Hormonal Proteins and Peptides*, vol. 2, p. 46, Academic Press (New York), 1973; and E. Atherton and R. C. Sheppard, *Solid-phase Peptide Synthesis: A Practical Approach*, IRL Press at Oxford University Press (Oxford, 1989). For the use of solid-phase methodology in the preparation of non-peptide molecules see Leznoff, C. C., *Acc. Chem. Res.*, 1978, 11, 327–333. For the use of polymeric reagents in functional group transformations, see A. Akelah and D. C. Sherrington, Application of Functionalized Polymers in Organic Synthesis, *Chem Rev.*, 1981, 81, 557–587 and W. T. Ford and E. C. Blossey, Polymer Supported Reagents, Polymer supported Catalysts, and Polymer Supported Coupling Reactions, in *Preparative Chemistry using Supported Reagents*, Pierre Laszlo, ed., Academic Press, Inc., 193–212 (1987). For the use of polymeric reagents in oxidation reactions, see J. M. J. Frechet et al., *J. Org. Chem.*, 1978, 43, 2618 and G. Cainelli et al., *J. Am. Chem. Soc.*, 1976, 98, 6737. For the use of polymeric reagents in halogenation reactions see J. M. J. Frechet et al., *J. Macromol. Sci. Chem.*, 1977, A-11, 507 and D. C. Sherrington et al., *Eur. Polym. J.*, 1977, 13, 73. For the use of polymeric reagents in epoxidation reactions, see J. M. J. Frechet et al., *Macromolecules*, 1975, 8, 130 and C. R. Harrison et al., *J. Chem. Soc. Chem. Commun.*, 1974, 1009. For the use of polymeric reagents in acylation reactions see M. B. Shambhu et al., *Tet. Lett.*, 1973, 1627 and M. B. Shambhu et al., *J. Chem. Soc. Chem. Commun.*, 1974, 619. For the use of polymeric reagents in Wittig reactions, see S. V. McKinley et al., *J. Chem. Soc. Chem. Commun.*, 1972, 134.

Polymeric reagents also have found widespread use in combinatorial and parallel synthesis and for preparing combinatorial and parallel synthesis libraries. For discussions, see F. Balkenhohl et al., *Angew. Chem. Int. Ed. Engl.*, 1996, 35, 2288–2337; L. A. Thompson et al., *Chem Rev.*, 1996, 96, 555–600; S. R. Wilson and A. W. Czarnik, *Combinatorial Chemistry*, John Wiley (N.Y.), 1997; D. Obrecht and J. M. Villalgordo, *Solid-Supported Combinatorial and Parallel Synthesis of Small-Molecular-Weight Compound Libraries*, Elsevier Science Ltd. (UK), 1998.

However, analytical methodology for monitoring and quantifying reactions using polymeric reagents is not as developed as the solid-phase techniques themselves. In general, samples are cleaved from the solid support and analyzed by conventional means, such as TLC, IR and $^1$H NMR. Removal of samples from the solid support is time consuming and may result in alteration of the reaction product. Therefore, the development of analytical methods for quantitating and monitoring chemical transformations of resin-bound samples is central to the advancement of solid-phase synthetic techniques.

Reported developments related to the analysis of resin-bound samples using fluorine NMR include the use of $^{19}$F NMR to characterize products resulting from linking fluorine-containing aromatic compounds to TentaGel resin (Svensson et al., *Tetrahedron Lett.*, 1996, 37, 7649); the use of $^{19}$F NMR and magic angle spinning $^{19}$F NMR to monitor the nucleophilic displacement of fluorine from 4-fluoro-3-nitrobenzamide linked to Rink resin (Shapiro et al., *Tetrahedron Lett.*, 1996, 37, 4671); the use of fluorinated analogs of p-hydroxymethylbenzoic acid, 3-[4-(hydroxymethylphenyl)]alkanoic acid, and 4-(hydroxymethyl)phenoxyacetic acid linkers for monitoring solid-phase synthesis using gel-phase $^{19}$F NMR (Svensson et al., *Tetrahedron Lett.*, 1998, 39, 7193–7196); and a method of quantifying resin loading using gel phase $^{19}$F NMR (Stones et al., *Tetrahedron Lett.*, 1998, 39, 4875–4878).

SUMMARY OF THE INVENTION

This invention concerns methods for monitoring and quantifying solid-phase reactions using solid-phase synthetic reagents in which one or more fluorine atoms are permanently incorporated as an internal standard, thereby making it possible to directly quantify and monitor resin loading and subsequent solid-phase reactions by $^{19}$F NMR.

This invention is also understood to include both single and multiple-step solid-phase reactions. In the latter case, monitoring and quantifying reactions may be accomplished at one or more steps in a synthetic sequence.

Advantages arising from the practice of this invention include: direct observation of reaction yields and kinetics of polymer-supported moieties; rapid sample preparation requiring only washing a solid-phase reaction product to remove soluble $^{19}$F labeled species prior to the analysis; high analytical sensitivity due to the high natural abundance of the $^{19}$F isotope; large $^{19}$F NMR spectral dispersion (about 200 ppm); simple spectra comprising a single resonance for each non-equivalent $^{19}$F nucleus; rapid analysis (spectral acquisition typically within <5 minutes) using standard NMR hardware; the method is suited to high throughput analysis.

This invention is further directed, in general, to a method using $^{19}$F NMR spectroscopy to quantitate or monitor polymerization reactions and chemical modifications of polymeric compounds. To effect this method, it is necessary that fluorine-containing monomers, reagents or both are employed in the polymerization or chemical modification processes.

In order to calculate the amounts of reagents for use in subsequent reactions and for optimization of the subsequent chemistry, it is necessary to determine the loading of the fluorine-containing solid-phase reaction product.

Accordingly, in its principal aspect, this invention is directed to a method of quantitating a solid-phase reaction, this method comprising the steps of:

(a) reacting a solid-phase reaction component or a fluorine-containing solid-phase reaction component with a reactant or fluorine-containing reactant to form a fluorine-containing solid-phase reaction product;

(b) obtaining a $^{19}$F NMR spectrum of the fluorine-containing solid-phase reaction product; and (c) comparing the integral corresponding to the fluorine-containing solid-phase reaction product $^{19}$F resonance to the integral corresponding to a standard $^{19}$F resonance.

In another aspect, this invention is directed to a fluorine-containing solid-phase reaction component comprising a known quantity of fluorine, which reaction component is prepared by reacting a solid-phase reaction component with a quantity of a fluorine-containing reactant.

BRIEF DESCRIPTION OF THE DRAWINGS

FIG. 4 shows $^{19}$F resonances for 4-hydroxy-2,3,5,6-tetrafluorobenzamidomethyl-copoly(styrene-1%-divinylbenzene)resin at about −146 and −164 ppm. In addition, the $^{19}$F spectrum also contains resonances at about −140, −144 and −153 ppm, corresponding to an unexpected side product resulting from coupling of 4-hydroxy-2,3,5,6-tetrafluorobenzamidomethyl-copoly(styrene-1%-divinylbenzene)-resin with a second molecule of 2,3,5,6-tetrafluoro-4-hydroxybenzoic acid to form the corresponding ester. FIG. 4 illustrates the usefulness of the methods described herein to detect and monitor formation of an undesired side product and thereby allow the development of synthetic methodology to maximize formation of the desired 4-hydroxy-2,3,5,6-tetrafluorobenzamidomethyl-copoly(styrene-1%-divinylbenzene)-resin.

FIG. 7 illustrates both the signal-to-noise ratios and the linewidths observed for copoly(styrene-4-fluorostyrene-4-chloromethylstyrene-1%-divinylbenzene)-resin having a fluorine content of approximately 0.72 percent by weight.

DETAILED DESCRIPTION OF THE INVENTION

Definitions of Terms

Figure 1:
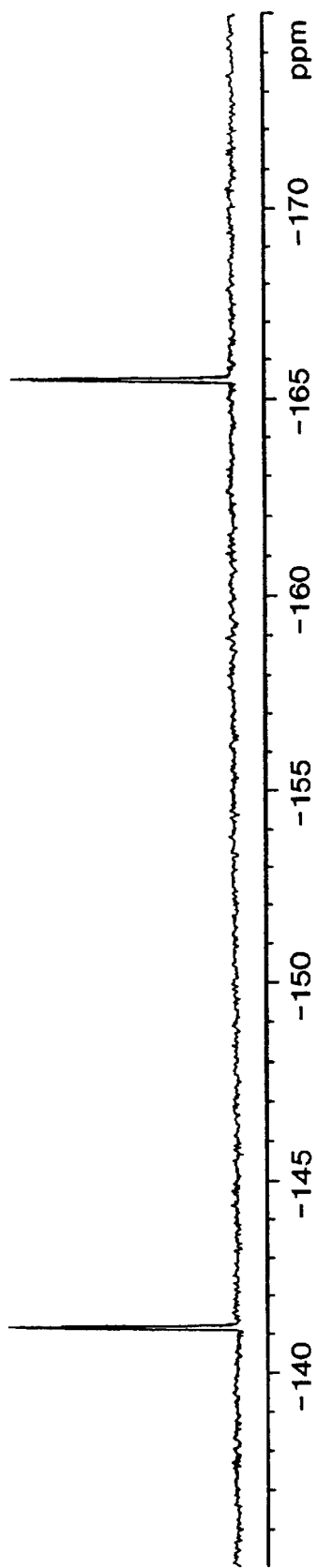
FIG. 1 is the $^{19}$F MAS NMR spectrum of 2,3,5,6-tetrafluoro-4-hydroxybenzoic acid.
Figure 2:
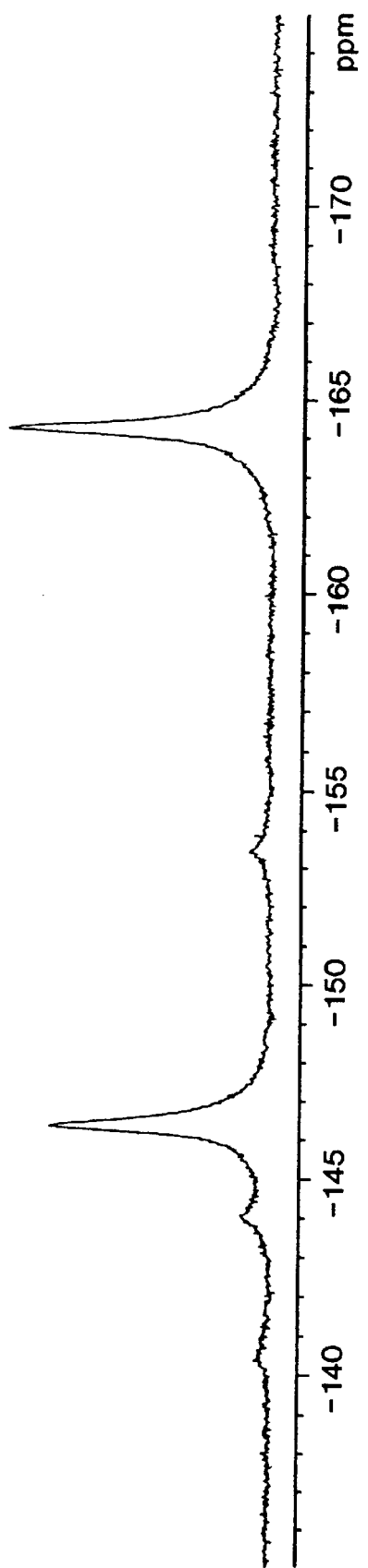
FIG. 2 is the $^{19}$F MAS NMR spectrum of 4-hydroxy-2,3,5,6-tetrafluorobenzamidomethylcopoly(styrene-1%-divinylbenzene)-resin.
Figure 3:
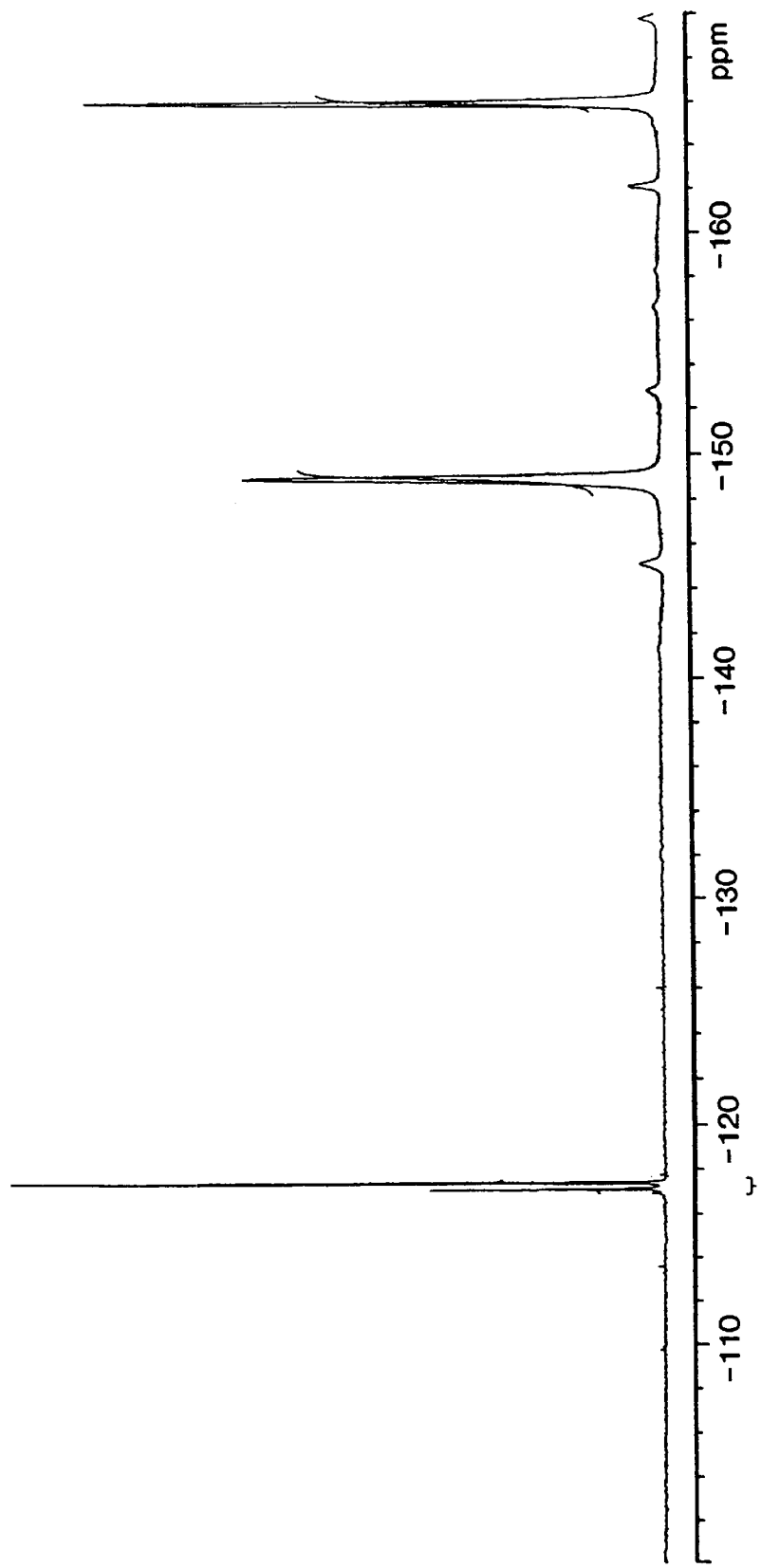
FIG. 3 is the $^{19}$F MAS NMR spectrum of a mixture of 3-fluorobenzamide and 4-hydroxy-2,3,5,6-tetrafluorobenzamidomethyl-copoly(styrene-1%-divinylbenzene)resin.
Figure 4:
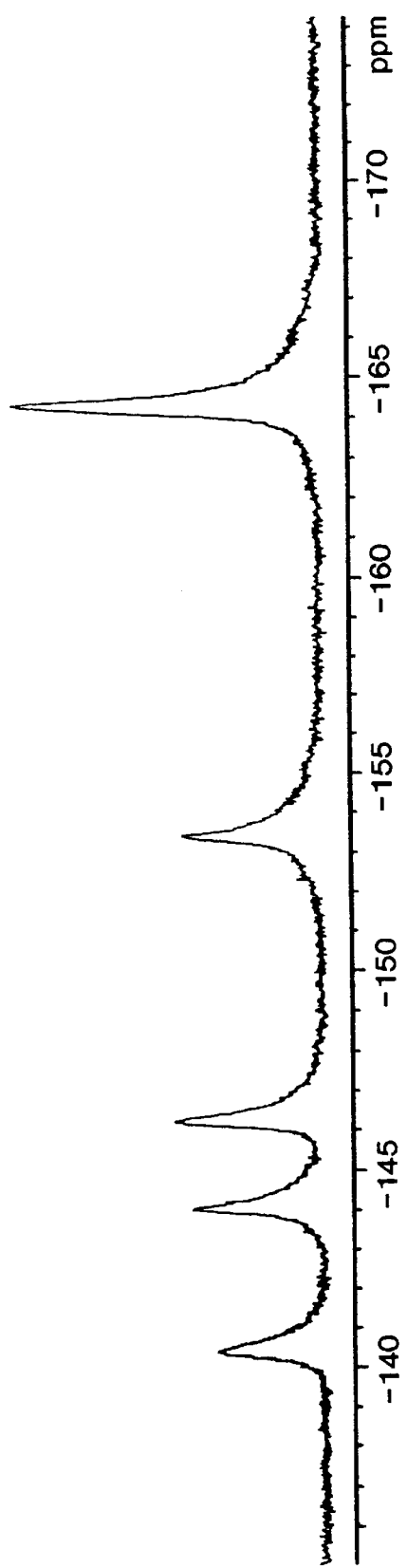
FIG. 4 is the $^{19}$F MAS NMR spectrum of a product mixture resulting from the coupling of aminomethyl resin and 2,3,5,6-tetrafluoro-4-hydroxybenzoic acid in the presence of diisopropylcarbodiimide (DIC) and 4-dimethylaminopyridine (DMAP).
Figure 5:
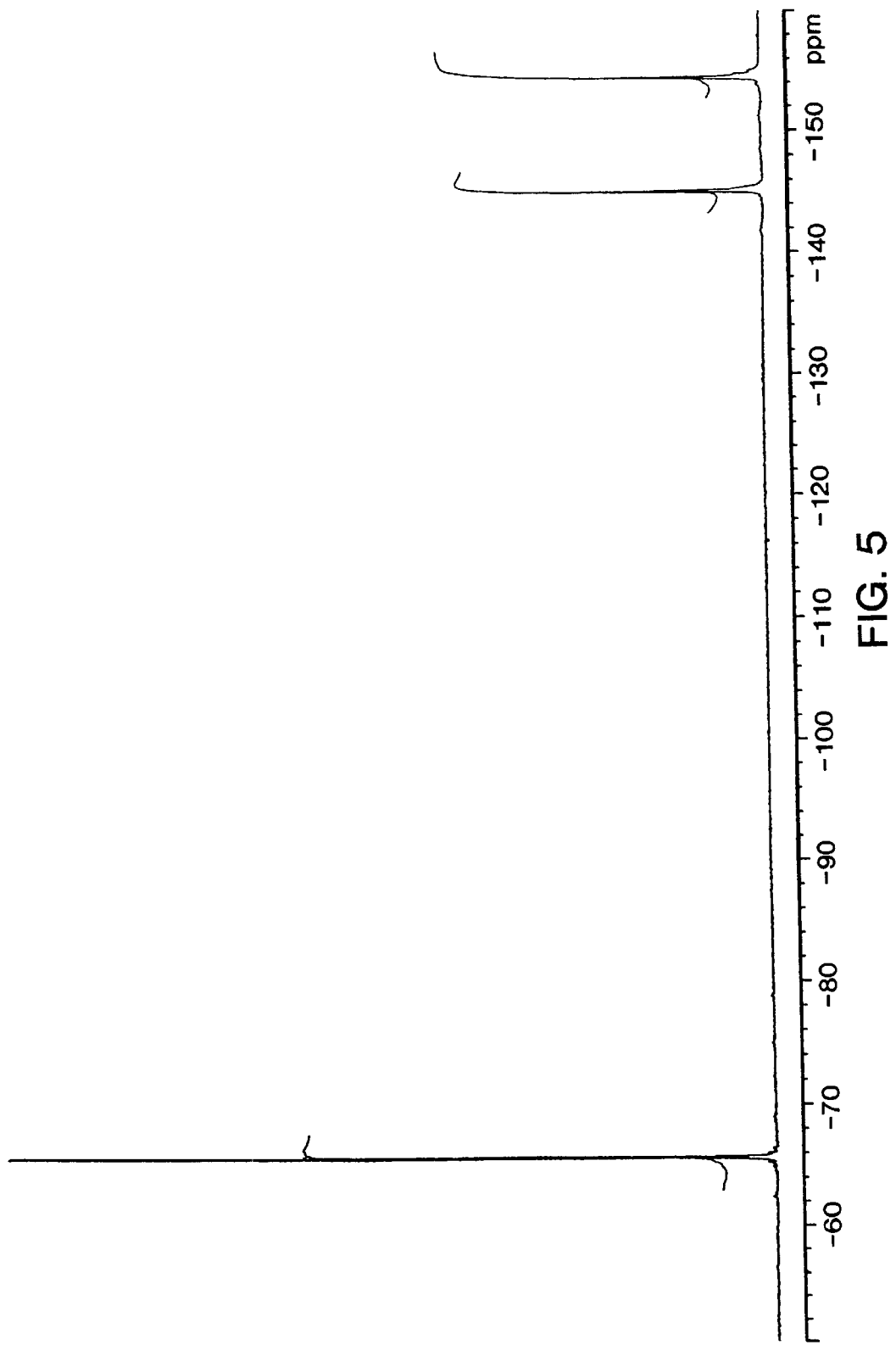
FIG. 5 is the $^{19}$F MAS NMR spectrum of 4-[1-(4-trifluoromethylphenyl)-2,5-dimethylpyrrol-4-oyl]oxy-2,3,5,6-tetrafluorobenzamidomethyl-copoly(styrene-1%-divinylbenzene) resin.

The following abbreviations are used throughout the application:
allyloxycarbonyl (Alloc); tert-butoxycarbonyl (BOC); bis (2-oxo-3-oxazolidinyl)-phosphonic chloride (BOP-Cl); benzyloxycarbonyl (CBZ); N,N'-dicyclohexylcarbodiimide (DCC); N,N'-diisopropylcarbodiimide (DIC); 4-dimethylaminopyridine (DMAP); N,N-dimethylformamide (DMF); dimethylsulfoxide (DMSO); high-performance liquid chromatography (HPLC); infrared spectroscopy (IR or FTIR); 1-hydroxybenzotriazole (HOBT); magic angle spinning (MAS); m-chloroperbenzoic acid (MCPBA); 2-methoxyethoxymethyl (MEM); methoxymethyl (MOM); mass spectrometry (MS); methylthiomethyl (MTM); nuclear magnetic resonance spectroscopy (NMR); 2-(1H-benzotriazole-1-yl)-1,1,3,3-tetramethyluronium tetrafluoroborate (TBTU); tetrahydrofuran (THF); thin layer chromatography (TLC); tetramethylethylenediamine (TMEDA); trimethylsilyl (TMS); tert-butyldimethylsilyl (TBDMS). Additional abbreviations are defined in the description of the invention.

As used above and throughout the description of the invention, the following terms, unless otherwise indicated, shall be understood to have the following meanings:

"Solid support" means a substrate which is inert to the reagents and reaction conditions described herein, as well as being substantially insoluble in the media used. Representative solid supports include inorganic substrates such as kieselguhr, silica gel, and controlled pore glass; organic polymers including polystyrene, including 1–2% copolystyrene divinyl benzene (gel form) and 20–40% copolystyrene divinyl benzene (macro porous form), polypropylene, polyethylene glycol, polyacrylamide, cellulose, and the like; and composite inorganic/polymeric compositions such as polyacrylamide supported within a matrix of kieselguhr particles. See J. M. Stewart and J. D. Young, *Solid-phase Peptide Synthesis*, 2nd. Ed., Pierce Chemical Co. (Chicago, Ill., 1984).

In addition, "solid support" includes a solid support as described above which is affixed to a second inert support such as the pins described in Technical Manual, Multipin™ SPOC, Chiron Technologies (1995) and references therein which comprise a detachable polyethylene- or polyproylene-based head grafted with an amino functionalized methacrylate copolymer and an inert stem.

In addition, "solid support" includes polymeric supports such as the polyethylene glycol supports described by Janda et al., *Proc. Natl. Acad. Sci USA*, 92, 6419–6423 (1995) and S. Brenner, WO 95/16918, which are soluble in many solvents but can be precipitated by the addition of a precipitating solvent.

In addition, "solid support" includes a solid support as defined above which further includes one or more fluorine atoms.

"Linking group" and "linker" mean a group through which the functional groups suitable for reaction with a reactant or fluorine-containing reactant may be covalently linked to the solid support. The linking group is substantially inert to the reagents and reaction conditions described herein.

"Fluorine-containing subunit" means a compound which contains at least one fluorine atom and which contains functionality suitable for forming a covalent bond to the solid-phase reaction component, and at least one additional functional group suitable for reaction with a reactant or fluorine-containing reactant to form the fluorine-containing solid-phase reaction product. The additional functional group(s) may be protected with a suitable protecting group so as to avoid interference with formation of the bond to the solid-phase reaction component. "Fluorine-containing solid-phase reaction product" means a product formed by reaction between a solid-phase reaction component or a fluorine-containing solid-phase reaction component and a reactant or fluorine-containing reactant, wherein the fluorine-containing solid-phase reaction product contains at least one fluorine atom. The fluorine-containing solid-phase reaction product is prepared by reacting a fluorine-containing solid-phase reaction component as defined herein with a reactant as defined herein or with a fluorine-containing reactant as defined herein, or by reaction of a solid-phase reaction component as defined herein with a fluorine-containing reactant as defined herein. The fluorine-containing solid-phase reaction product may contain functional groups suitable for further solid-phase reactions, in which case the further solid-phase reactions may be quantified using the methods described herein.

"Solid-phase reaction component" means a solid support as defined herein which contains a plurality of reactive sites containing functional groups suitable for reaction with a fluorine-containing reactant to form a fluorine-containing solid-phase reaction product. In the case of multiple-step solid-phase synthesis the solid-phase reaction component can include appended moieties and their attendant reactive sites which contain functional groups suitable for reaction with a reactant or a fluorine-containing reactant to form a fluorine-containing solid-phase reaction product.

"Fluorine-containing solid-phase reaction component" means a solid-phase reaction component as defined herein which contains at least one fluorine atom.

"Reactant" means a compound which contains functionality suitable for forming a covalent bond to a solid-phase reaction component or to a fluorine-containing solid-phase reaction component to form a fluorine-containing solid-phase reaction product. In addition to possessing functionality suitable for forming the covalent bond to the solid-phase reaction component, the reactant may contain at least one additional functional group suitable for reaction with additional reactants while attached to the solid support. The functional group may be protected with a suitable protecting group so as to avoid interference with formation of the bond to the solid-phase reaction component.

"Fluorine-containing reactant" means a reactant as defined herein which contains at least one fluorine atom in addition to the functionality suitable for forming a covalent bond to the solid-phase reaction component, such that reaction of the fluorine-containing reactant with a solid-phase reaction component or fluorine-containing solid-phase reaction component results in formation of a fluorine-containing solid-phase reaction product in which at least one fluorine atom is incorporated in the fluorine-containing solid-phase reaction product through the fluorine-containing reactant. In addition to possessing functionality suitable for forming the covalent bond to the solid-phase reaction component, the fluorine-containing reactant may contain at least one additional functional group suitable for reaction with additional reactants while attached to the solid support. The functional group may be protected with a suitable protecting group so as to avoid interference with formation of the bond to the solid-phase reaction component.

"Resin loading" means the fraction of reactive sites on the solid-phase reaction component which react with the reactant or fluorine-containing reactant to form the fluorine-containing solid-phase reaction product (i.e., the fraction of reactive sites which are "loaded" by the reactant or fluorine-containing reactant).

"Standard" refers to a fluorine-containing entity which, when a known amount is combined with a fluorine-containing solid-phase reaction product, permits quantification of the formation of the fluorine-containing solid-phase reaction product by comparison of the $^{19}F$ integral of the fluorine-containing solid-phase reaction product and the $^{19}F$ integrals of the standard. The standard may be either "internal," in which case the standard is physically incorporated in a known amount into the solid-phase reaction component, or "external," in which case a known amount of a fluorine-containing standard compound is present with a sample of the fluorine-containing solid-phase reaction product.

"Magic angle spinning" (MAS) is an NMR technique in which the sample tube is oriented at a defined angle relative to the magnetic field. Magic angle spinning is used in solid state and gel phase NMR to remove line broadening caused by chemical-shift anisotropy. The "magic angle" is about 54.7°. For general discussions of MAS NMR, see Koenig, J. L., *Spectroscopy of Polymers*; American Chemical Society, Washington, D.C., 1992 and Fitch et al., *J. Org. Chem.*, 1994, 59, 7955, and references cited therein.

"Amine protecting group" means an easily removable group which is known in the art to protect an amino group against undesirable reaction during synthetic procedures and to be selectively removable. The use of N-protecting groups is well known in the art for protecting amino and other reactive nitrogen-containing groups against undesirable reactions during a synthetic procedure, and many such protecting groups are known. See, for example, T. H. Greene and P. G. M. Wuts, *Protective Groups in Organic Synthesis*, 2nd edition, John Wiley & Sons, New York (1991), the contents of which are hereby incorporated herein by reference. Preferred N-protecting groups are acyl, including formyl, acetyl, chloroacetyl, trichloroacetyl, o-nitrophenylacetyl, o-nitrophenoxyacetyl, trifluoroacetyl, acetoacetyl, 4-chlorobutyryl, isobutyryl, o-nitrocinnamoyl, picolinoyl, acylisothiocyanate, aminocaproyl, benzoyl and the like, and acyloxy, including methoxycarbonyl, 9-fluorenylmethoxycarbonyl, 2,2,2-trifluoroethoxycarbonyl, 2-trimethylsilylethxoycarbonyl, vinyloxycarbonyl, t-butyloxycarbonyl (BOC), 1,1-dimethylpropynyloxycarbonyl, benzyloxycarbonyl (CBZ), p-nitrophenylsulfinyl, p-nitrobenzyloxycarbony, 2,4-dichlorobenzyloxycarbonyl, allyloxycarbonyl (Alloc), and the like.

"Carboxylic acid protecting group" and "acid protecting group" mean an easily removable group which is known in the art to protect a carboxylic acid (—CO$_2$H) group against undesirable reaction during synthetic procedures and to be selectively removable. The use of carboxylic acid protecting groups is well known in the art, and many such protecting groups are known. See, for example, T. H. Greene and P. G. M. Wuts, Protective Groups in Organic Synthesis, 2nd edition, John Wiley & Sons, New York (1991), the contents of which are hereby incorporated herein by reference. Examples of carboxylic acid protecting groups include ester groups, such as methoxymethyl, methylthiomethyl, tetrahydropyranyl, benzyloxymethyl, substituted and unsubstituted phenacyl, 2,2,2-trichloroethyl, tert-butyl, cinnamyl, substituted and unsubstituted benzyl, trimethylsilyl, allyl, and the like, and amide and hydrazide groups, including N,N-dimethyl, 7-nitroindolyl, hydrazide, N-phenylhydrazide, and the like. Especially preferred carboxylic acid protecting groups are tert-butyl and benzyl.

"Hydroxy protecting group" means an easily removable group which is known in the art to protect a hydroxy group against undesirable reaction during synthetic procedures and to be selectively removable. The use of hydroxy protecting groups is well known in the art, and many such protecting groups are known. See, for example, T. H. Greene and P. G. M. Wuts, Protective Groups in Organic Synthesis, 2nd edition, John Wiley & Sons, New York (1991), the contents of which are hereby incorporated herein by reference. Examples of hydroxy protecting groups include ether moieties, such as methyl; substituted methyl ether moieties, such as methoxymethyl (MOM), methylthiomethyl (MTM), 2-methoxyethoxymethyl (MEM), bis(2-chloroethoxy) methyl, tetrahydropyranyl (THP), tetrahydrothiopyranyl, 4-methoxytetrahydropyranyl, 4-methoxytetrahydrothiopyranyl, tetrahydrofuranyl, tetrahydrothiofuranyl, and the like; substituted ethyl ether moieties, such as 1-ethoxyethyl, 1-methyl-1-methoxyethyl, 2-(phenylselenyl)ethyl, t-butyl, allyl, benzyl, o-nitrobenzyl, triphenylmethyl, α-naphthyldiphenyl methyl,p-methoxyphenyldiphenylmethyl, 9-(9-phenyl-10-oxo) anthranyl (tritylone), and the like; silyl ether moieties, such as trimethylsilyl (TMS), isopropyldimethylsilyl, t-butyldimethylsilyl (TBDMS), t-butyldiphenylsilyl, tribenzylsilyl, tri-p-xylylsilyl, triisopropylsilyl, and the like; ester moieties, such as formate, acetate, trichloroacetate, phenoxyacetate, isobutyrate, pivaloate, adamantoate, benzoate, 2,4,6-trimethylbenzoate, and the like; and carbonate moieties, such as methyl, 2,2,2-trichloroethyl, allyl, p-nitrophenyl, benzyl,p-nitrobenzyl, S-benzyl thiocarbonate, and the like.

"Amino acid" means an amino acid selected from the group consisting of natural and unnatural amino acids as defined herein.

"Natural amino acid" means an α-amino acid selected from-the group consisting of alanine (ALA), valine (VAL), leucine (LEU), isoleucine (ILE), proline (PRO), phenylalanine (PHE), tryptophan (TRP), methionine (MET), glycine (GLY), serine (SER), threonine (THR), cysteine (CYS), tyrosine (TYR), asparagine (ASN), glutamine (GLN), lysine (LYS), arginine (ARG), histidine (HIS), aspartic acid (ASP) and glutamic acid (GLU).

"Unnatural amino acid" means an amino acid for which there is no nucleic acid codon. Examples of unnatural amino acids include, for example, the D-isomers of the natural α-amino acids as indicated above; aminobutyric acid, 3-aminoisobutyric acid, norvaline, β-ALA, 2-aminoadipic acid, 3-aminoadipic acid, 2-aminobutyric acid, γ-aminobutyric acid (GABA), 6-aminocaproic acid, 2,4-diaminobutryic acid, α-aminopimelic acid, trimethylsilyl-ALA, allo-isoleucine, norleucine, tert-LEU, citrulline, ornithine, 2,2'-diaminopimelic acid, 2,3-diaminopropionic acid, α- or β—Nal, cyclohexyl-ALA, hydroxyproline, sarcosine, and the like; cyclic amino acids; $N^α$-alkylated amino acids, such as $N^α$-methylglycine, $N^α$-ethylglycine and $N^α$-ethylasparagine; and amino acids in which the α-carbon bears two side-chain substituents.

"Equivalent amino acid" means an amino acid which may be substituted for another amino acid in a given peptide-without any appreciable loss of function. In making such changes, substitutions of like amino acids is made on the basis of relative similarity of side chain substituents, for example regarding size, charge, hydrophilicity, hydropathicity and hydrophobicity.

"Peptide" and "polypeptide" mean a polymer in which the monomers are natural or unnatural amino acid residues joined together through amide bonds. The term "peptide backbone" means the series of amide bonds through which the amino acid residues are joined. The term "amino acid residue" means the individual amino acid units incorporated into the peptides or polypeptides.

"Aliphatic" means a radical derived from a non aromatic C—H bond by removal of the hydrogen atom. The aliphatic radical may be further substituted by additional aliphatic or aromatic radicals as defined herein. Representative aliphatic groups include alkyl, alkenyl, alkynyl, cycloalkyl, cycloalkenyl, heterocyclyl, heterocyclenyl, aralkenyl, aralkyloxyalkyl, aralkyloxycarbonylalkyl, aralkyl, aralkynyl, aralkyloxyalkenyl, heteroaralkenyl, heteroaralkyl, heteroaralkyloxyalkenyl, heteroaralkyloxyalkyl, heteroaralkynyl, fused arylcycloalkyl, fused heteroarylcycloalkyl, fused arylcycloalkenyl, fused heteroarylcycloalkenyl, fused arylheterocyclyl, fused heteroarylheterocyclyl, fused arylheterocyclenyl, fused heteroarylheterocyclenyl, and the like.

"Aromatic" means a radical containing one or more groups of atoms in a cyclic array that contains clouds of delocalized π electrons above and below the plane of the atoms; furthermore, the π clouds must contain a total of (4q+2)π electrons, where q is any positive integer. "Aromatic" includes both aryl and heteroaryl rings as defined herein. The aryl or heteroaryl ring may be further substituted by additional aliphatic or aromatic radicals as defined herein. Representative aromatic groups include aryl, fused cycloalkenylaryl, fused cycloalkylaryl, fused heterocyclylaryl, fused heterocyclenylaryl, heteroaryl, fused cycloalkylheteroaryl, fused cycloalkenylheteroaryl, fused heterocyclenylheteroaryl, fused heterocyclylheteroaryl, and the like.

"Acyl" means an H—CO— or alkyl-CO— group wherein the alkyl group is as herein described. Preferred acyls contain a lower alkyl. Exemplary acyl groups include formyl, acetyl, propanoyl, 2-methylpropanoyl, butanoyl and palmitoyl.

"Acylamino" is an acyl-NH— group wherein acyl is as defined herein.

"Alkenoyl" means an alkenyl-CO— group wherein alkenyl is as defined herein.

"Alkenyl" means a straight or branched aliphatic hydrocarbon group of 2 to about 15 carbon atoms which contains at least one carbon-carbon double bond. Preferred alkenyl groups have 2 to about 12 carbon atoms; more preferred alkenyl groups have 2 to about 4 carbon atoms. The alkenyl group is optionally substituted with one or more alkyl group substituents as defined herein. Representative alkenyl groups include ethenyl, propenyl, n-butenyl, i-butenyl, 3-methylbut-2-enyl, n-pentenyl, heptenyl, octenyl, cyclohexylbutenyl and decenyl.

"Alkenylene" denotes a divalent group derived from a straight or branched chain hydrocarbon containing at least one carbon-carbon double bond. Representative alkenylene include —CH=CH—, —CH$_2$CH=CH—, —C(CH$_3$)=CH—, —CH$_2$CH=CHCH$_2$—, and the like.

"Alkenyloxy" means an alkenyl-O— group wherein the alkenyl group is as herein described. Representative alkenyloxy groups include allyloxy or 3-butenyloxy.

"Alkoxy" means an alkyl-O— group wherein the alkyl group is as defined herein. Representative alkoxy groups include methoxy, ethoxy, n-propoxy, i-propoxy, n-butoxy, heptoxy, and the like.

"Alkoxyalkylenyl" means an alkyl-O-alkylene- group wherein alkyl and alkylene are as defined herein. Representative alkoxyalkylenyl groups include methoxyethyl, ethoxymethyl, n-butoxymethyl and cyclopentylmethyloxyethyl.

"Alkoxyalkoxy" means an alkyl-O-alkylene-O— group. Representative alkoxyalkoxy groups include methoxymethoxy, methoxyethoxy, ethoxyethoxy, and the like.

"Alkoxycarbonyl" means an ester group; i.e. an alkyl-O—CO— group wherein alkyl is as defined herein. Representative alkoxycarbonyl groups include methoxycarbonyl, ethoxycarbonyl, t-butyloxycarbonyl, and the like.

"Alkoxycarbonylalkyl" means an alkyl-O—CO-alkylene- group wherein alkyl and alkylene are as defined herein. Representative alkoxycarbonylalkyl groups include methoxycarbonylmethyl, and ethoxycarbonylmethyl, methoxycarbonyl ethyl, and the like.

"Alkyl" means an aliphatic hydrocarbon group which may be straight or branched having about 1 to about 20 carbon atoms in the chain. Preferred alkyl groups have 1 to about 12 carbon atoms in the chain. Branched means that one or more lower alkyl groups such as methyl, ethyl or propyl are attached to a linear alkyl chain. "Lower alkyl" means about 1 to about 4 carbon atoms in the chain which may be straight or branched. The alkyl may be substituted with one or more "alkyl group substituents" which may be the same or different, and include halo, cycloalkyl, hydroxy, alkoxy, amino, carbamoyl, acylamino, aroylamino, carboxy, alkoxycarbonyl, aralkyloxycarbonyl, or heteroaralkyloxycarbonyl. Representative alkyl groups include methyl, trifluoromethyl, cyclopropylmethyl, cyclopentylmethyl, ethyl, n-propyl, i-propyl, n-butyl, t-butyl, n-pentyl, 3-pentyl, methoxyethyl, carboxymethyl, methoxycarbonylethyl, benzyloxycarbonylmethyl, and pyridylmethyloxycarbonylmethyl.

"Alkylene" means a straight or branched bivalent hydrocarbon chain of 1 to about 20 carbon atoms. Alkylene may be substituted by one or more alkyl group substituents as defined herein. Preferred alkylene groups are the lower alkylene groups having 1 to about 4 carbon atoms. Representative alkylene groups include methylene, ethylene, and the like.

"Alkylsulfinyl" means an alkyl-SO— group wherein the alkyl group is as defined above. Preferred alkylsulfinyl groups are those wherein the alkyl group is lower alkyl.

"Alkylsulfonyl" means an alkyl-SO$_2$— group wherein the alkyl group is as defined herein. Preferred alkylsulfonyl groups are those wherein the alkyl group is lower alkyl.

"Alkylsulfonylcarbamoyl" means an alkyl-SO$_2$—NH—CO— group wherein alkyl group is defined herein. Preferred alkylsulfonylcarbamoyl groups are those wherein the alkyl group is lower alkyl.

"Alkylthio" means an alkyl-S— group wherein the alkyl group is as defined herein. Preferred alkylthio groups are those wherein the alkyl group is lower alkyl. Representative alkylthio groups include methylthio, ethylthio, i-propylthio, heptylthio, and the like.

"Alkynyl" means a straight or branched aliphatic hydrocarbon group of 2 to about 15 carbon atoms which contains at least one carbon-carbon triple bond. Preferred alkynyl groups have 2 to about 12 carbon atoms. More preferred alkynyl groups contain 2 to about 4 carbon atoms. "Lower alkynyl" means alkynyl of 2 to about 4 carbon atoms. The alkynyl group may be substituted by one or more alkyl group substituents as defined herein. Representative alkynyl groups include ethynyl, propynyl, n-butynyl, 2-butynyl, 3-methylbutynyl, n-pentynyl, heptynyl, octynyl, decynyl, and the like.

"Alkynylene" refers to a divalent group derived by the removal of two hydrogen atoms from a straight or branched chain acyclic hydrocarbon group containing a carbon-carbon triple bond. Representative alkynylene include

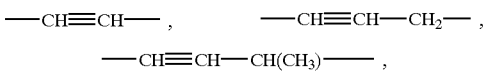

and the like.

"Alkynyloxy" means an alkynyl-O— group wherein the alkynyl group is as defined herein. Representative alkynyloxy groups include propynyloxy, 3-butynyloxy, and the like.

"Alkynyloxyalkyl" means alkynyl-O-alkylene- group wherein alkynyl and alkylene are as defined herein.

"Amidino" or "amidine" means a group of formula

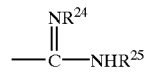

wherein $R^{24}$ is selected from hydrogen; cyano; alkyl; nitro; amino; $R^{26}O_2C$—; $R^{26}O$—; and $R^{26}C(O)$—, wherein $R^{26}$ is aralkyl or heteroaralkyl; and $R^{25}$ is selected from hydrogen; alkyl; aralkyl; and heteroaralkyl.

"Amino" means a group of formula $Y^1Y^2N$— wherein $Y^1$ and $Y^2$ are independently hydrogen; acyl; or alkyl, or $Y^1$ and $Y^2$, taken together with the N atom to which $Y^1$ and $Y^2$ are linked, form a 4 to 7 membered azaheterocyclyl or azaheterocyclenyl group. Representative amino groups include amino (H$_2$N—), methylamino, dimethylamino, diethylamino, piperidino and the like.

"Aminoalkyl" means an amino-alkylene- group wherein amino and alkylene are as defined herein. Representative aminoalkyl groups include aminomethyl, aminoethyl, dimethylaminomethyl, and the like.

"Aralkenyl" means a aryl-alkenylene- group wherein aryl and alkenylene are as define herein. Preferred aralkenyl groups contain a lower alkenylene moiety. A representative aralkenyl group is 2-phenethenyl.

"Aralkyloxy" means an aralkyl-O— group wherein aralkyl is as defined herein. Representative aralkoxy groups include benzyloxy, naphth-1-ylmethoxy, naphth-2-ylmethoxy, and the like.

"Aralkyloxyalkyl" means an aralkyl-O-alkylene- group wherein aralkyl and alkylene are as defined herein. A representative aralkoxyalkyl group is benzyloxyethyl.

"Aralkyloxycarbonyl" means an aralkyl-O—CO— group wherein aralkyl is as defined herein. A representative aralkoxycarbonyl group is benzyloxycarbonyl.

"Aralkyloxycarbonylalkyl" means an aralkoxycarbonyl-alkylene- group wherein aralkoxycarbonyl and alkylene are as defined herein. Representative aralkoxycarbonylalkyl groups include benzyloxycarbonylmethyl, and benzyloxycarbonylethyl.

"Aralkyl" means an aryl-alkylene- group wherein aryl and alkylene are as defined herein. Preferred aralkyl groups contain a lower alkylene group. Representative aralkyl groups include benzyl, 2-phenethyl, naphthlenemethyl, and the like.

"Aralkyloxyalkenyl" means an aralkyl-O-alkenylene- group wherein aralkyl and alkenylene are as defined herein. A representative aralkyloxyalkenyl group is 3-benzyloxyallyl.

"Aralkylsulfonyl" means an aralkyl-SO$_2$— group wherein aralkyl is as defined herein.

"Aralkylsulfinyl" means an aralkyl-SO— group wherein aralkyl is as defined herein.

"Aralkylthio" means an aralkyl-S— group wherein aralkyl is as defined herein. A representative aralkylthio group is benzylthio.

"Aroyl" means an aryl-CO— group wherein aryl is as defined herein. Representative aroyl groups include benzoyl, naphth 1-oyl and naphth-2-oyl.

"Aryl" means an aromatic monocyclic or multicyclic ring system of 6 to about 14 carbon atoms, preferably of about 6 to about 10 carbon atoms. The aryl group is optionally substituted with one or more "ring system substituents," which may be the same or different, and are as defined herein. Representative aryl groups include phenyl and naphthyl.

"Aralkynyl" means an aryl-alkynylene- group wherein aryl and alkynylene are as defined herein. Representative aralkynyl groups include phenylacetylenyl and 3-phenylbut-2-ynyl.

"Aryldiazo" means an aryl-N=N— group wherein aryl is as defined herein. Representative aryldiazo groups include phenyldiazo and naphthyldiazo.

"Arylcarbamoyl" means an aryl-NHCO— group, wherein aryl is as defined herein.

"Carbamyl" means a group of formula $Y^1Y^2NCO$— wherein $Y^1$ and $Y^2$ are as defined herein. Representative carbamyl groups include carbamyl ($H_2NCO$—), dimethylaminocarbamoyl ($Me_2NCO$—), and the like.

"Chemical bond" means a direct bond.

"Fused arylcycloalkenyl" means a radical derived from a fused aryl and cycloalkenyl as defined herein by removal of hydrogen atom from the cycloalkenyl portion. Preferred fused arylcycloalkenyl groups are those wherein the aryl is phenyl and the cycloalkenyl consists of about 5 to 6 ring atoms. The fused arylcycloalkenyl is optionally substituted by one or more ring system substituents, wherein "ring system substituent" is as defined herein. Representative fused arylcycloalkenyl include 1,2-dihydronaphthylene, indene, and the like, in which the bond to the parent moiety is through a non-aromatic carbon atom.

"Fused cycloalkenylaryl" means a radical derived from a fused aryl and cycloalkenyl as defined herein by removal of hydrogen atom from the aryl portion. Representative fused cycloalkenylaryl groups are as described herein for a fused arylcycloalkenyl, except that the bond to the parent moiety is through an aromatic carbon atom.

"Fused arylcycloalkyl" means a radical derived from a fused aryl and cycloalkyl as defined herein by removal of a hydrogen atom from the cycloalkyl portion. Preferred fused arylcycloalkyl groups are those wherein the aryl is phenyl and the cycloalkyl consists of about 5 to 6 ring atoms. The fused arylcycloalkyl group is optionally substituted by one or more ring system substituents, wherein "ring system substituent" is as defined herein. Representative fused arylcycloalkyl groups include 1,2,3,4-tetrahydronaphthyl, and the like, in which the bond to the parent moiety is through a non-aromatic carbon atom.

"Fused cycloalkylaryl" means a radical derived from a fused aryl and cycloalkyl as defined herein by removal of a hydrogen atom from the aryl portion. Representative fused cycloalkylaryl groups are as described herein for a fused arylcycloalkyl radical, except that the bond to the parent moiety is through an aromatic carbon atom.

"Fused arylheterocyclenyl" means a radical derived from a fused aryl and heterocyclenyl as defined herein by removal of a hydrogen atom from the heterocyclenyl portion. Preferred fused arylheterocyclenyl groups are those wherein the aryl is phenyl and the heterocyclenyl consists of about 5 to 6 ring atoms. The prefix aza, oxa or thia before the heterocyclenyl portion of the fused arylheterocyclenyl means that at least a nitrogen, oxygen or sulfur atom, respectively, is present as a ring atom. The fused arylheterocyclenyl group is optionally substituted by one or more ring system substituents, wherein "ring system substituent" is as defined herein. The nitrogen or sulphur atom of the heterocyclenyl portion of the fused arylheterocyclenyl is optionally oxidized to the corresponding N-oxide, S-oxide or S,S-dioxide. Representative fused arylheterocyclenyl groups include 3H-indolinyl, 1H-2-oxoquinolyl, 2H-1-oxoisoquinolyl, 1,2-dihydroquinolinyl, 3,4-dihydroquinolinyl, 1,2-dihydroisoquinolinyl, 3,4-dihydroisoquinolinyl, and the like, in which the bond to the parent moiety is through a non-aromatic carbon or nitrogen atom capable of such.

"Fused heterocyclenylaryl" means a radical derived from a fused aryl and heterocyclenyl as defined herein by removal of a hydrogen atom from the aryl portion. Representative fused heterocyclenylaryl groups are as defined herein for a fused arylheterocyclenyl radical, except that the bond to the parent moiety is through an aromatic carbon atom.

"Fused arylheterocyclyl" means a radical derived from a fused aryl and heterocyclyl as defined herein by removal of a hydrogen atom from the heterocyclyl portion. Preferred fused arylheterocyclyl groups are those wherein the aryl is phenyl and the heterocyclyl consists of about 5 to 6 ring atoms. The prefix aza, oxa or thia before heterocyclyl means that at least a nitrogen, oxygen or sulfur atom, respectively, is present as a ring atom. The fused arylheterocyclyl group is optionally substituted by one or more ring system substituents, wherein "ring system substituent" is as defined herein. The nitrogen or sulphur atom of the heterocyclyl portion of the fused arylheterocyclyl group is optionally oxidized to the corresponding N-oxide, S-oxide or S,S-dioxide. Representative preferred fused aryllheterocyl ring systems include indolinyl, 1,2,3,4-tetrahydroisoquinoline, 1,2,3,4-tetrahydroquinoline, 1H-2,3-dihydroisoindolyl, 2,3-dihydrobenz[f]isoindolyl, 1,2,3,4-tetrahydrobenz[g]isoquinolinyl, and the like, in which the bond to the parent moiety is through a non-aromatic carbon or nitrogen atom.

"Fused heterocyclylaryl" means a radical derived from a fused aryl and heterocyclyl as defined herein by removal of a hydrogen atom from the heterocyclyl portion. Representative preferred fused heterocyclylaryl ring systems are as described for fused arylheterocyclyl, except that the bond to the parent moiety is through an aromatic carbon atom.

"Carboxy" means a HO(O)C— group (i.e. a carboxylic acid moiety).

"Carboxyalkyl" means a HO(O)C-alkylene- group wherein alkylene is as defined herein. Representative carboxyalkyls include carboxymethyl and carboxyethyl.

"Cycloalkyloxy" means a cycloalkyl-O— group wherein cycloalkyl is as defined herein. Representative cycloalkyloxy groups include cyclopentyloxy, cyclohexyloxy, and the like.

"Cycloalkyl" means a non-aromatic mono- or multicyclic ring system of about 3 to about 10 carbon atoms, preferably of about 5 to about 10 carbon atoms. Preferred cycloalkyl rings contain about 5 to 6 ring atoms. The cycloalkyl is optionally substituted with one or more "ring system substituents" which may be the same or different, and are as defined herein. Representative monocyclic cycloalkyl groups include cyclopentyl, cyclohexyl, cycloheptyl, and the like. Representative multicyclic cycloalkyl groups include 1-decalin, norbornyl, adamantyl, and the like.

"Cycloalkenyl" means a non-aromatic mono- or multicyclic ring system of about 3 to about 10 carbon atoms, preferably of about 5 to about 10 carbon atoms, which contains at least one carbon-carbon double bond. Preferred cycloalkylene rings contain about 5 to 6 ring atoms. The cycloalkenyl is optionally substituted with one or more "ring system substituents," which may be the same or different, and are as defined herein. Representative monocyclic cycloalkenyl groups include cyclopentenyl, cyclohexenyl, cycloheptenyl, and the like. A representative multicyclic cycloalkenyl is norbornylenyl.

"Cycloalkylenyl" means a bivalent, saturated carbocyclic group having about 4 to about 8 carbon atoms. Preferred cycloalkylenyl groups include 1,2-, 1,3-, or 1,4-cis or trans-cyclohexanylene.

"Diazo" means a bivalent —N=N— radical.

"Ethylenyl" means a —CH=CH— group.

"Halo" or "halogen" mean fluoro, chloro, bromo, or iodo.

"Heteroaralkenyl" means a heteroaryl-alkenylene- group wherein heteroaryl and alkenylene are as defined herein. Preferred heteroaralkenyl groups contain a lower alkenylene moiety. Representative heteroaralkenyl groups include 4-pyridylvinyl, thienylethenyl, pyridylethenyl, imidazolylethenyl, pyrazinylethenyl, and the like.

"Heteroaralkyl" means a heteroaryl-alkylene- group wherein heteroaryl and alkylene are as defined herein. Preferred heteroaralkyl groups contain a lower alkylene group. Representative heteroaralkyl groups include thienylmethyl, pyridylmethyl, imidazolylmethyl, pyrazinylmethyl, and the like.

"Heteroaralkyloxy" means an heteroaralkyl-O— group wherein heteroaralkyl is as defined herein. A representative heteroaralkyloxy group is 4-pyridylmethyloxy.

"Heteroaralkyloxyalkenyl" means a heteroaralkyl-O-alkenylene- group wherein heteroaralkyl and alkenylene are as defined herein. A representative heteroaralkyloxyalkenyl group is 4-pyridylmethyloxyallyl.

"Heteroaralkyloxyalkyl" means a heteroaralkyl-O-alkylene- group wherein heteroaralkyl and alkylene are as defined herein. A representative heteroaralkyloxyalkyl group is 4-pyridylmethyloxyethyl.

"Heteroaralkynyl" means an heteroaryl-alkynylene- group wherein heteroaryl and alkynylene are as defined herein. Preferred heteroaralkynyl groups contain a lower alkynylene moiety. Representative heteroaralkynyl groups include pyrid-3-ylacetylenyl, quinolin-3-ylacetylenyl, 4-pyridylethynyl, and the like.

"Heteroaroyl" means an means a heteroaryl-CO— group wherein heteroaryl is as defined herein.

Representative heteroaroyl groups include thiophenoyl, nicotinoyl, pyrrol-2-ylcarbonyl, pyridinoyl, and the like.

"Heteroaryl" means an aromatic monocyclic or multicyclic ring system of about 5 to about 14 ring atoms, preferably about 5 to about 10 ring atoms, in which one or more of the atoms in the ring system is/are element(s) other than carbon, for example, nitrogen, oxygen or sulfur. Preferred heteroaryls contain about 5 to about 6 ring atoms. The "heteroaryl" may also be substituted by one or more "ring system substituents," which may be the same or different, and are as defined herein. The prefix aza, oxa or thia before heteroaryl means that at least a nitrogen, oxygen or sulfur atom, respectively, is present as a ring atom. A nitrogen atom of a heteroaryl may be oxidized to the corresponding N-oxide. Representative heteroaryls include pyrazinyl, furanyl, thienyl, pyridyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyridazinyl, quinoxalinyl, phthalazinyl, imidazo[1,2-a]pyridine, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, "Heteroaryldiazo" means an heteroaryl-N=N— group wherein heteroaryl is as defined herein.

"Fused heteroarylcycloalkenyl" means a radical derived from a fused heteroaryl and cycloalkenyl, wherein the heteroaryl and the cycloalkenyl are as defined herein, by removal of a hydrogen atom from the cycloalkenyl portion. Preferred fused heteroarylcycloalkenyl groups are those wherein the heteroaryl and the cycloalkenyl each contain about 5 to 6 ring atoms. The prefix aza, oxa or thia before heteroaryl means that at least a nitrogen, oxygen or sulfur atom, respectively, is present as a ring atom. The fused heteroarylcycloalkenyl is optionally substituted by one or more ring system substituents, wherein "ring system substituent" is as defined herein. The nitrogen atom of the heteroaryl portion of the fused heteroarylcycloalkenyl is optionally oxidized to the corresponding N-oxide. Representative fused heteroarylcycloalkenyl groups include 5,6-dihydroquinolyl, 5,6-dihydroisoquinolyl, 5,6-dihydroquinoxalinyl, 5,6-dihydroquinazolinyl, 4,5-dihydro-1H-benzimidazolyl, 4,5-dihydrobenzoxazolyl, and the like, in which the bond to the parent moiety is through a non-aromatic carbon atom.

"Fused cycloalkenylheteroaryl" means a radical derived from a fused heteroaryl and cycloalkenyl, wherein the heteroaryl and the cycloalkenyl are as defined herein, by removal of a hydrogen atom from the heteroaryl portion. Representative fused cycloalkenylheteroaryl groups are as described herein for fused heteroarylcycloalkenyl groups, except that the bond to the parent moiety is through an aromatic carbon atom.

"Fused heteroarylcycloalkyl" means a radical derived from a fused heteroaryl and cycloalkyl, wherein the heteroaryl and the cycloalkyl are as defined herein, by removal of a hydrogen atom from the cycloalkyl portion. Preferred fused heteroarylcycloalkyl groups are those wherein the heteroaryl portion thereof consists of about 5 to about 6 ring atoms and the cycloalkyl consists of about 5 to 6 ring atoms. The prefix aza, oxa or thia before heteroaryl means that at least a nitrogen, oxygen or sulfur atom is present, respectively, as a ring atom. The fused heteroarylcycloalkyl group is optionally substituted by one or more ring system substituents, wherein "ring system substituent" is as defined herein. The nitrogen atom of the heteroaryl portion of the fused heteroarylcycloalkyl is optionally oxidized to the corresponding N-oxide. Representative fused heteroarylcycloalkyl groups include 5,6,7,8-tetrahydroquinolinyl, 5,6,7,8-tetrahydroisoquinolyl, 5,6,7,8-tetrahydroquinoxalinyl, 5,6,7,8-tetrahydroquinazolyl, 4,5,6,7-tetrahydro-1H-benzimidazolyl, 4,5,6,7-tetrahydrobenzoxazolyl, 1H-4-oxa-1,5-diazanaphthalen-2-onyl, 1,3-dihydroimidizole-[4,5]-pyridin-2-onyl, and the like, in which the bond to the parent moiety is through a non-aromatic carbon atom.

"Fused cycloalkylheteroaryl" means a radical derived from a fused heteroaryl and cycloalkyl, wherein the heteroaryl and the cycloalkyl are as defined herein, by removal of a hydrogen atom from the heteroaryl portion. Representative fused cycloalkylheteroaryl groups are as described herein for fused heteroarylcycloalkyl, except that the bond to the parent moiety is through an aromatic carbon atom.

"Fused heteroarylheterocyclenyl" means a radical derived from a fused heteroaryl and heterocyclenyl, wherein the heteroaryl and the heterocyclenyl are as defined herein, by the removal of a hydrogen atom from the heterocyclenyl portion. Preferred fused heteroarylheterocyclenyl groups are those wherein the heteroaryl portion thereof consists of about 5 to 6 ring atoms and the heterocyclenyl portion consists of about 5 to 6 ring atoms. The prefix aza, oxa or thia before heteroaryl or heterocyclenyl means that at least a nitrogen, oxygen or sulfur atom is present respectively as a ring atom. The fused heteroarylheterocyclenyl group is optionally substituted by one or more ring system substituents, wherein "ring system substituent" is as defined herein. The nitrogen atom of the heteroaryl portion of the fused heteroarylheterocyclenyl group is optionally oxidized to the corresponding N-oxide. The nitrogen or sulphur atom of the heterocyclenyl portion of the fused heteroarylheterocyclenyl group is optionally oxidized to the corresponding N-oxide, S-oxide or S,S-dioxide. Representative fused heteroarylheterocyclenyl groups include 7,8-dihydro[1,7]naphthyridinyl, 1,2-dihydro[2,7]naphthyridinyl, 6,7-dihydro-3H-imidazo[4,5-c]pyridyl, 1,2-dihydro-1,5-naphthyridinyl, 1,2-dihydro-1,6-naphthyridinyl, 1,2-dihydro-1,7-naphthyridinyl, 1,2-dihydro-1,8-naphthyridinyl, 1,2-dihydro-2,6-naphthyridinyl, and the like, in which the bond to the parent moiety is through a non aromatic carbon or nitrogen atom.

"Fused heterocyclenylheteroaryl" means a radical derived from a fused heteroaryl and heterocyclenyl, wherein the heteroaryl and the heterocyclenyl are as defined herein, by the removal of a hydrogen atom from the heteroaryl portion. Representative fused heterocyclenylheteroaryl groups are as described herein for fused heteroarylheterocyclenyl, except that the bond to the parent moiety is through an aromatic carbon atom.

"Fused heteroarylheterocyclyl" means a radical derived from a fused heteroaryl and heterocyclyl, wherein the heteroaryl and the heterocyclyl are as defined herein, by removal of a hydrogen atom from the heterocyclyl portion. Preferred fused heteroarylheterocyclyl groups are those wherein the heteroaryl portion thereof consists of about 5 to 6 ring atoms and the heterocyclyl portion consists of about 5 to 6 ring atoms. The prefix aza, oxa or thia before the heteroaryl or heterocyclyl portion of the fused heteroarylheterocyclyl means that at least a nitrogen, oxygen or sulfur atom respectively is present as a ring atom. The fused heteroarylheterocyclyl group is optionally substituted by one or more ring system substituents, wherein "ring system substituent" is as defined herein. The nitrogen atom of the heteroaryl portion of the fused heteroarylheterocyclyl group is optionally oxidized to the corresponding N-oxide. The nitrogen or sulphur atom of the heterocyclyl portion of the fused heteroarylheterocyclyl is optionally oxidized to the corresponding N-oxide, S-oxide or S,S-dioxide. Representative fused heteroarylheterocyclyl groups include 2,3-dihydro-1H pyrrol[3,4-b]quinolin-2-yl, 1,2,3,4-tetrahydrobenz[b][1,7]naphthyridin-2-yl, 1,2,3,4-tetrahydrobenz[b][1,6]naphthyridin-2-yl, 1,2,3,4-tetrahydro-9H-pyrido[3,4-b]indol-2-yl, 1,2,3,4-tetrahydro-9H-pyrido[4,3-b]indol-2-yl, 2,3,-dihydro-1H-pyrrolo[3,4-b]indol-2-yl, 1H-2,3,4,5-tetrahydroazepino[3,4-b]indol-2-yl, 1H-2,3,4,5-tetrahydroazepino[4,3-b]indol-3-yl, 1H-2,3,4,5-tetrahydroazepino[4,5-b]indol-2-yl, 5,6,7,8-tetrahydro[1,7]napthyridinyl, 1,2,3,4-tetrahydro[2,7]napthyridinyl, 2,3-dihydro[1,4]dioxino[2,3-b]pyridyl, 2,3-dihydro[1,4]dioxino[2,3-b]pryidyl, 3,4-dihydro-2H-1-oxa[4,6]diazanaphthalenyl, 4,5,6,7-tetrahydro-3H-imidazo[4,5-c]pyridyl, 6,7-dihydro[5,8]diazanaphthalenyl, 1,2,3,4-tetrahydro[1,5]napthyridinyl, 1,2,3,4-tetrahydro[1,6]napthyridinyl, 1,2,3,4-tetrahydro[1,7]napthyridinyl, 1,2,3,4-tetrahydro[1,8]napthyridinyl, 1,2,3,4-tetrahydro[2,6]napthyridinyl, and the like, in which the bond to the parent moiety is through a non-aromatic carbon atom.

"Fused heterocyclylheteroaryl" means a radical derived from a fused heteroaryl and heterocyclyl, wherein the heteroaryl and the heterocyclyl are as defined herein, by removal of a hydrogen atom from the heteroaryl portion. Representative fused heterocyclylheteroaryl groups are as described herein for fused hetararylheterocyclyl, except that the bond to the parent moiety is through an aromatic carbon atom.

"Heteroarylsulphonylcarbamoyl" means a heteroaryl-$SO_2$—NH—CO— group wherein heteroaryl is as defined herein.

"Heterocyclenyl" means a non-aromatic monocyclic or multicyclic ring system of about 3 to about 10 ring atoms, preferably about 5 to about 10 ring atoms, in which one or more of the atoms in the ring system is/are element(s) other than carbon, for example nitrogen, oxygen or sulfur atoms, and which contains at least one carbon-carbon double bond or carbon-nitrogen double bond. Preferred heterocyclenyl rings contain about 5 to 6 ring atoms. The prefix aza, oxa or thia before heterocyclenyl means that at least a nitrogen, oxygen or sulfur atom, respectively, is present as a ring atom. The heterocyclenyl group may be optionally substituted by one or more ring system substituents, wherein "ring system substituent" is as defined herein. The nitrogen or sulphur atom of the heterocyclenyl is optionally oxidized to the corresponding N-oxide, S-oxide or S,S-dioxide. Representative monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Representative oxaheterocyclenyl groups include 3,4-dihydro-2H-pyran, dihydrofuranyl, fluorodihydrofuranyl, and the like. A representative multicyclic oxaheterocyclenyl group is 7-oxabicyclo[2.2.1]heptenyl. Representative monocyclic thiaheterocyclenyl rings include dihydrothiophenyl, dihydrothiopyranyl, and the like "Heterocyclyl" means a non-aromatic saturated monocyclic or multicyclic ring system of about 3 to about 10 ring atoms, preferably about 5 to about 10 ring atoms, in which one or more of the atoms in the ring system is/are element(s) other than carbon, for example nitrogen, oxygen or sulfur. Preferred heterocyclyl groups contain about 5 to 6 ring atoms. The prefix aza, oxa or thia before heterocyclyl means that at least a nitrogen, oxygen or sulfur atom, respectively, is present as a ring atom. The heterocyclyl group is optionally substituted by one or more "ring system substituents," which may be the same or different, and are as defined herein. The nitrogen or sulphur atom of the heterocyclyl group is optionally oxidized to the corresponding N-oxide, S-oxide or S,S-dioxide. Representative monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Heterocyclylalkyl" means a heterocyclyl-alkylene-group wherein heterocyclyl and alkylene groups are as defined herein. Preferred heterocyclylalkyl groups contain a lower alkylene moiety. A representative heteroaralkyl group is tetrahydropyranylmethyl.

"Heterocyclylalkyloxyalkyl" means a heterocyclylalkyl-O-alkylene group wherein heterocyclylalkyl and alkylene are as defined herein. A representative heterocyclylalkyloxyalkyl group is tetrahydropyranylmethyloxymethyl.

"Heterocyclyloxy" means a heterocyclyl-O— group wherein heterocyclyl is as defined herein. Representative heterocyclyloxy groups include quinuclidyloxy, pentamethylenesulfideoxy, tetrahydropyranyloxy, tetrahydrothiophenyloxy, pyrrolidinyloxy, tetrahydrofuranyloxy, 7-oxabicyclo[2.2.1]heptanyloxy, hydroxytetrahydropyranyloxy, hydroxy-7-oxabicyclo[2.2.1]heptanyloxy, and the like.

"Hydroxyalkyl" means an alkyl group as defined herein substituted with one or more hydroxy groups. Preferred hydroxyalkyl groups contain lower alkyl. Representative hydroxyalkyl groups include hydroxymethyl and 2-hydroxyethyl.

"N-oxide" means a

group.

"Phenoxy" means a phenyl-O— group wherein the phenyl ring is optionally substituted with one or more ring system substituents as defined herein.

"Phenylene" means a -phenyl—group wherein the phenyl ring is optionally substituted with one or more ring system substituents as defined herein.

"Phenylthio" means a phenyl-S— group wherein the phenyl ring is optionally substituted with one or more ring system substituents as defined herein.

"Pyridyloxy" means a pyridyl-O— group wherein the pyridyl ring is optionally substituted with one or more ring system substituents as defined herein.

"Ring system substituent" means a substituent attached to a ring system, which replaces hydrogen on an aromatic or non-aromatic ring system. Ring system substituents are selected from the group consisting of aryl, heteroaryl, aralkyl, heteroaralkyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, aryldiazo, heteroaryldiazo, amidino, amino, aminoalkyl, carbamyl and sulfamyl. When a ring system is saturated or partially saturated, the "ring system substituent" further comprises methylene ($H_2C=$), oxo ($O=$) and thioxo ($S=$).

"Sulfamyl" means a group of formula $Y^1Y^2NSO_2$— wherein $Y^1$ and $Y^2$ are as defined herein. Representative sulfamyl groups are aminosulfamoyl ($H_2NSO_2$—) and dimethylaminosulfamoyl ($Me_2NSO_2$—).

Preferred Embodiments

In a preferred aspect of this invention, this invention is directed to the use of $^{19}F$ NMR spectroscopy to monitor and quantitate solid-phase reactions, and fluorine-containing solid-phase reagents useful therefor.

In a preferred aspect of this invention, this invention is directed to a method of quantitating a solid-phase reaction, this method comprising the steps of:

(a) reacting a solid-phase reaction component or a fluorine-containing solid-phase reaction component with a reactant or fluorine-containing reactant to form a fluorine-containing solid-phase reaction product;

(b) obtaining a $^{19}F$ NMR spectrum of the fluorine-containing solid-phase reaction product; and (c) comparing the integral corresponding to the fluorine-containing solid-phase reaction product $^{19}F$ resonance to the integral corresponding to a standard $^{19}F$ resonance.

A preferred internal standard for use in the method of this invention is a fluorine-containing solid-phase reaction component prepared by reaction of a quantity of solid-phase reaction component with a quantity of fluorine-containing reactant, such that a known quantity of fluorine is incorporated into the resulting fluorine-containing solid-phase reaction component which retains a fraction of its original reactive sites. Preparation of such internal standard is illustrated by Example 14 (vide infra).

A preferred fluorine-containing reactant suitable for reaction with the solid-phase reaction component to form the fluorine-containing solid-phase reaction component is selected from the group consisting of: bis(2,2,2-trifluoroethyl)amine, 3,5-bis(trifluoromethyl)benzoyl chloride, 4-fluorobenzoyl chloride, 4-fluorobenzylamine, 4-fluorobenzenesulfonyl chloride, 4-fluorobenzaldehyde, 4-fluorophenylchloroformate, 3-fluorophenyl isocyanate, 4-fluorophenylisothiocyanate, trifluoroacetic anhydride, trifluoromethanesulfonic anhydride, 4-(trifluoromethyl)benzylamine, 4-(trifluoromethyl)benzyl bromide, 4-(trifluoromethyl)phenylhydrazine, 4-(trifluoromethyl)phenyl isocyanate, 4-(trifluoromethyl)thiophenol, 1H, 1H, 2H, 2H-perfluorodecyldimethylchlorosilane, 2,2,2-trifluoroethanesulfonyl chloride, 2,2,2,-trifluoroethanol, 4-fluorophenol, 4-fluorobenzoic acid, and the like.

A preferred fluorine-containing reactant is 4-fluorophenol. In a preferred aspect of this invention, the internal standard for use in the method of this invention is a fluorine-containing solid-phase reaction component of formula II

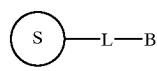

wherein

is a solid support optionally containing one or more fluorine atoms;

L is a chemical bond or a linking group optionally containing one or more fluorine atoms, provided that at least one of the solid support and the linking group contains at least one fluorine atom; and B is a functional group suitable for reaction with a reactant or fluorine-containing reactant to form a fluorine-containing solid-phase reaction product.

In a more preferred aspect of this invention, the fluorine-containing solid-phase reaction component for use in this invention is a fluorine-containing solid-phase reaction component of formula III

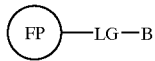

wherein

is a solid support containing one or more fluorine atoms;

LG is a chemical bond or a linking group optionally substituted by one or more fluorine atoms; and B is a functional group suitable for reaction with a reactant or fluorine-containing reactant to form a fluorine-containing solid-phase reaction product.

More preferred fluorine-containing solid-phase reaction components for use as internal standards according to the method of this invention have formula IV wherein

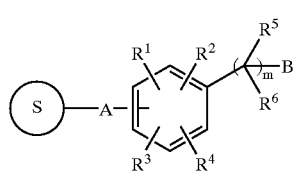

is a solid support;

L is a group of formula

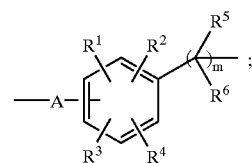

A is a chemical bond or is selected from

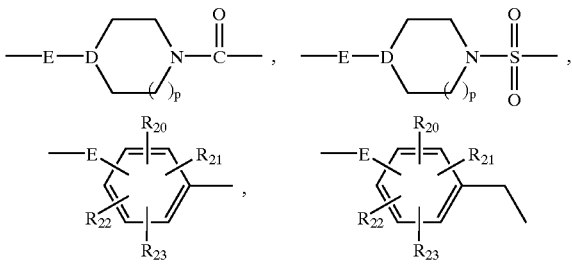

—E—C(O)—, —E—YC(O)—, —E—SO$_2$—, —E—NR$^7$SO$_2$—, —E—CHR$^7$—, —E—CHR$^7$Y— and —E—CHR$^7$YC(O)(CH$_2$)$_m$—;

E is a chemical bond,

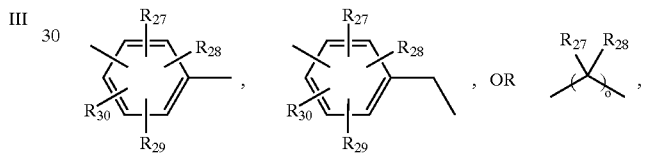

o is 1 to 5,
B is halogen, —NHP, —OW or —SO$_2$Z;
D is CH or N;
P is H or an amine protecting group;
W is —H, —NHP, —NPR$^9$, —NR$^{10}$C(O)Cl, —C(O)R$^9$, —C(O)NR$^{10}$R$^{11}$, —C(O)OR$^9$, —SO$_2$R$^9$, tripyrrolidinophosphonium or —C(O)-imidazol-1-yl;
Y is —O— or —NR$^8$—;
Z is —Cl, —OH, —OR, or —NR$^9$R$^{12}$;
R$^1$ is —F, or when one of R$^{16}$, R$^{17}$, R$^{18}$ and R$^{19}$ is F, R$^1$ is —H, alkyl, alkoxy, halogen, —CN or —NO$_2$;
R$^2$, R$^3$ and R$^4$ are independently —H, alkyl, alkoxy, halogen, —CN or —NO$_2$, or one of R$^2$ R$^3$ and R$^4$, taken together with one of R$^5$ and R$^6$ and the carbon atoms to which they are attached, define a group of formula

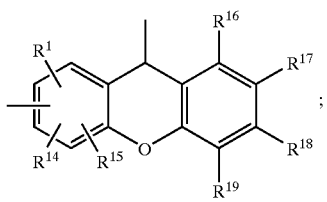

R$^5$ and R$^6$ are independently —H, alkyl, phenyl or phenyl substituted with one or more substituents selected from alkyl, alkoxy, halogen, nitrile and —NO$_2$;
R$^7$ and R$^8$ are independently —H or lower alkyl;

$R^9$ and $R^{13}$ are independently aliphatic or aromatic;
$R^{10}$ and $R^{11}$ are independently —H, aliphatic or aromatic;
$R^{12}$ is —CH$_2$R$^{13}$;
$R^{14}$, $R^{15}$, $R^{16}$, $R^{17}$, $R^{18}$, $R^{19}$, $R^{20}$, $R^{21}$, $R^{22}$, $R^{23}$ $R^{27}$, $R^{28}$, $R^{29}$, and $R^{30}$ are independently selected from —H, alkyl, alkoxy, halogen, —CN and —NO$_2$;
m is 0 or 1;
n is 1–6; and
p is 0, 1 or 2.

In a preferred aspect of this invention, the $^{19}$F NMR spectra are obtained using any $^{19}$F NMR technique, including magic angle spinning.

In a preferred aspect of this invention, the solid-phase reaction is quantified using an external standard.

In a more preferred aspect of this invention, the solid-phase reaction is quantitated using an internal standard comprising a fluorine-containing solid-phase reaction component as defined herein.

In order to determine resin loading using an external standard, a known quantity of a fluorine-containing standard compound is added as an external standard to a precisely determined amount of the fluorine-containing solid-phase reaction product. Suitable fluorine-containing standard compounds comprise any unreactive, soluble fluorinated substance. Preferred fluorine-containing standard compounds are 3-fluorobenzamide (3FB) and 4-(trifluoromethyl) benzamide (4TFB).

The $^{19}$F spectrum of this system consists of well resolved resonances corresponding to the fluorine-containing standard compound and the fluorine-containing solid-phase reaction component. Simple calculation using the integral values for the $^{19}$F signals of the fluorine-containing standard compound and the fluorine-containing solid-phase reaction component, and known quantities of fluorine-containing standard compound and the fluorine-containing solid-phase reaction component present in the sample gives the resin loading value.

The loading of fluorine-containing solid-phase reaction component in moles/gram resin ($\alpha$)determined by $^{19}$F NMR using an external standard has been verified by comparison to measurements of $\alpha$ using other techniques, such as elemental analysis. In order to determine resin loading using an internal standard, the loading of fluorine-containing solid-phase reaction product in moles/gram resin ($\alpha$) may be calculated using formula 1:

$$\alpha = \frac{xI_r}{yI_s} \cdot \frac{Q_s}{M_r} \qquad \text{(formula 1)}$$

where,
($\alpha$)=The loading of fluorine-containing solid-phase reaction product in moles/gram resin
$I_r$=Integral or intensity corresponding to the product resonance;
$I_s$=Integral or intensity of standard resonance;
x=Number of equivalent fluorine atoms in standard;
y=Number of equivalent fluorine atoms in product;
$Q_s$=Quantity in moles of the standard;
$M_r$=Mass in grams of the resin.

The determination of resin loading using an internal standard is determined as described above by comparing the integrals of the $^{19}$F resonance(s) of the internal standard with the $^{19}$F resonance(s) of the fluorine-containing solid-phase reaction product. Incorporation of $^{19}$F into the solid-phase reaction component to create the internal standard is discussed above.

Fluorine-containing solid-phase reaction components of formula II comprising a solid support and a fluorine-containing linking group are prepared by reacting a solid-phase reaction component as defined herein with a fluorine-containing subunit. The preparation of representative fluorine-containing solid-phase reaction components which incorporate fluorine-containing linking groups is shown in Examples 16 and 17.

In a preferred aspect of this invention, the solid-phase reaction components suitable for reaction with a fluorine-containing subunit to form the fluorine-containing solid-phase reaction component include polystyrene, aminomethyl polystyrene, Merrifield resin (chloromethylated polystyrene), hydroxymethyl resin, formyl polystyrene, sulfonylated polystyrene, carboxyl polystyrene, bromopolystyrene, and the like.

Fluorine-containing solid-phase reaction components of formula III are prepared by polymerization using methods known in the art so as to incorporate one or more fluorine-containing monomers into the solid support. Representative suitable fluorine-containing monomers include 4-fluorostyrene, 4-trifluoromethylstyrene, 2-fluoro-4-vinylbenzyl chloride and the like.

Preferred fluorine-containing solid-phase reaction components of formula III are prepared by copolymerizing mixtures of 4-fluorostyrene, styrene, 1,4-divinylbenzene and 4-vinylbenzyl chloride.

In a preferred aspect, the fluorine-containing solid-phase reaction component is prepared by reacting the solid-phase reaction component with about 0.05 to about 10.0 molar equivalents of the fluorine-containing reactant, more preferably, from about 0.05 to about 2.0 molar equivalents of fluorine-containing reactant.

The preparation of fluorine-containing solid-phase reaction components of formula IV above for use according to the method of this invention is described in the Schemes below. The preparation and use of fluorine-containing solid-phase reaction components of formula IV in which B is ONHP or ONPR$^9$ in the preparation of aldehyde, ketone, oxime, amine, and hydroxamic acid compounds is described in PCT/US97/23920, the contents of which are hereby incorporated herein by reference. The preparation and use of fluorine-containing solid-phase reaction components of formula IV in which B is —OW or —SO$_2$Z wherein W is —H, —NR$^{10}$C(O)Cl, —C(O)R$^9$, —C(O)NR$^{10}$R$^{11}$, —C(O)OR$^9$, —SO$_2$R$^9$ or —C(O)— imidazol-1-yl in the preparation of amides, peptides, hydroxamic acids, amines, urethanes, carbonates, carbamates, sulfonamides and $\alpha$-substituted carbonyl compounds is described in U.S. patent application Ser. No.: 60/090,558, filed Jun. 24, 1998, the contents of which are hereby incorporated herein by reference.

The preparation of the solid-phase reaction component of formula (3, 5)

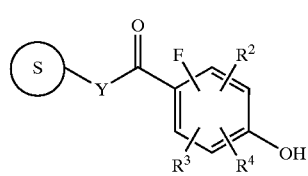

is shown in Scheme 1.

Scheme 1

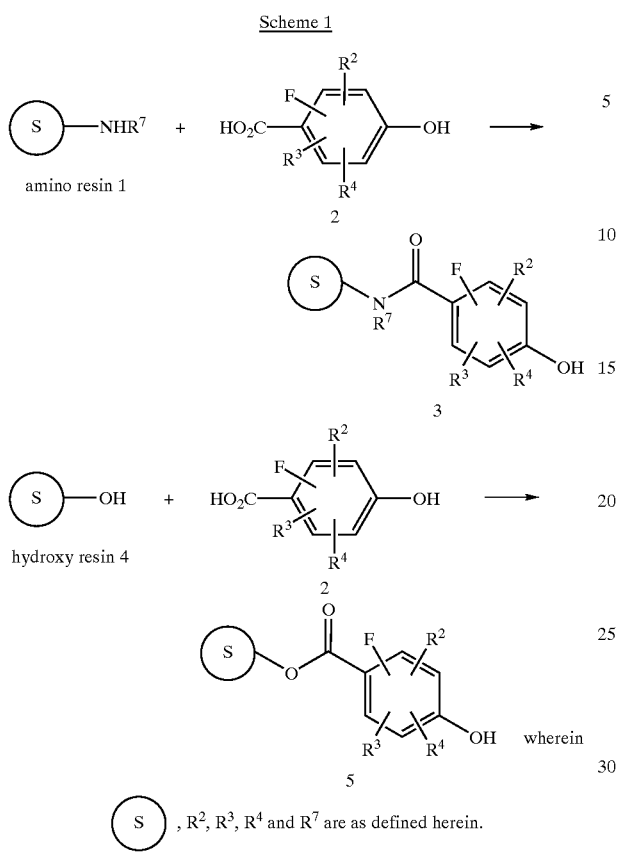

According to the foregoing Scheme 1, amino resin 1 or hydroxy resin 4 is coupled with the 4-hydroxyfluorobenzoic acid derivative 2 in a suitable organic solvent such as dichloromethane, DMF, DMSO or THF to form, respectively, the 4-hydroxy fluorine-containing solid-phase reaction component 3 or 4-hydroxyfluorobenzoyloxy resin component 5. Coupling times range from about 2 to about 24 hours, depending upon the amino resin and 4-hydroxyfluorobenzoic acid derivative to be coupled, activating agent, solvent and temperature. The coupling is accomplished at from about $-10°$ C. to about $50°$ C., preferably at about ambient temperature. The carboxylic acid moiety is activated with an appropriate activating agent (for a list of activating agents, with specific references, see Arrieta et al., Synn. Commun. 13, 471, 1983) such as isopropyl chloroformate in the presence of N-methylmorpholine, diisopropylcarbodiimide (DIC) in the presence of 1-hydroxybenzotriazole (HOBT), diisopropyl-carbodiimide (DIC) in the presence of 4-dimethylaminopyridine (DMAP), bis(2-oxo-3-oxazolidinyl)-phosphonic chloride (BOP-Cl) in the presence of triethylamine, bromotripyrrolidinophosphonium hexafluorophosphate (PyBroP™) in the presence of triethylamine (TEA), 2-(1H-benzotriazole-1-yl)-1,1,3,3-tetramethyluronium tetrafluoroborate (TBTU) in the presence of diisopropylethyl amine, N-hydroxysuccinimide in the presence of N,N'-dicyclohexylcarbodiimide (DCC), pyridinium salts-$Bu_3N$, phenyl dichlorophosphate $PhOPOCl_2$, 2-chloro-1,3,5-trinitrobenzene and pyridine, polyphosphate ester, chlorosulfonyl isocyanate $ClSO_2NCO$, chlorosilane, $MeSO_2Cl$—$Et_3N$, $PH_3P$—$CCl_4$—$Et_3N$, and the like.

A preferred amino resin 1 for preparing the 4-hydroxyfluorobenzamido resins 3 for use in the methods of this invention is aminomethyl polystyrene. Depending on the size of the particles, which are preferably in the range of about 75–250 mesh, aminomethyl polystyrene has loading ranges of from about 0.5 to about 1.2 mmol/g in the case of 75 mesh, and from about 0.1 to about 0.5 mmol/g in the case of 250 mesh, respectively. Aminomethyl polystyrene having a particle size of 75 mesh is preferred.

A preferred hydroxy resin 4 is hydroxymethyl resin.

In a preferred method of preparing the 4-hydroxyfluorobenzamido resin 3, a mixture of the 4-hydroxyfluorobenzoic acid derivative 2, aminomethyl polystyrene, diisopropylcarbodiimide (DIC) and 4-dimethylaminopyridine (DMAP) in anhydrous DMF is stirred at about ambient temperature for about 18 hours. The 4-hydroxyfluorobenzamido resin 3 is then filtered, washed with one or more solvents and dried.

The preparation of the solid-phase reaction component of formula

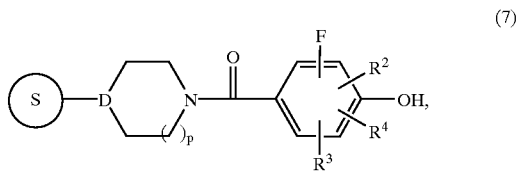

(7)

wherein D, p, $R^2$, $R^3$ and $R^4$ are defined herein, is shown in Scheme 2.

Scheme 2

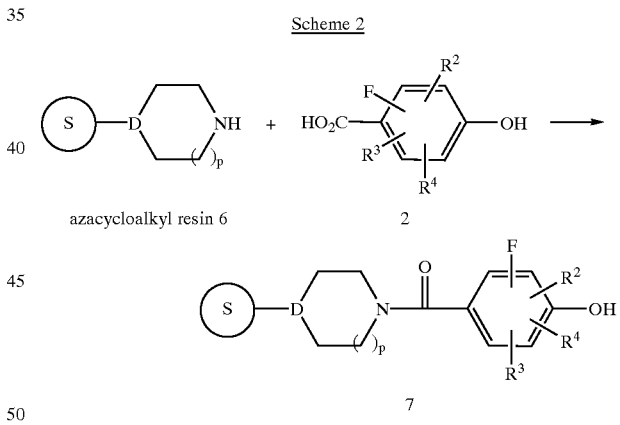

As shown in Scheme 2 above, coupling of the azacycloalkyl resin compound 6 with the 4-hydroxyfluorobenzoic acid compound 2 provides the 4-hydroxyfluorobenzoyl-azacycloalkyl resin compound 7. The coupling is accomplished using the reagents and conditions described in Scheme 1 above. A preferred azacycloalkyl resin compound is (piperidinomethyl) polystyrene, designated herein as

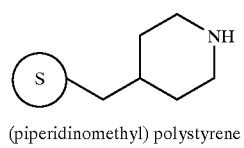

(piperidinomethyl) polystyrene

The preparation of the solid-phase reaction component of formula

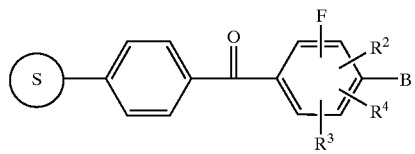

wherein B is F, OH, SO$_3$H or SO$_2$Cl and R$^2$, R$^3$ and R$^4$ are as defined herein, is shown in Scheme 3.

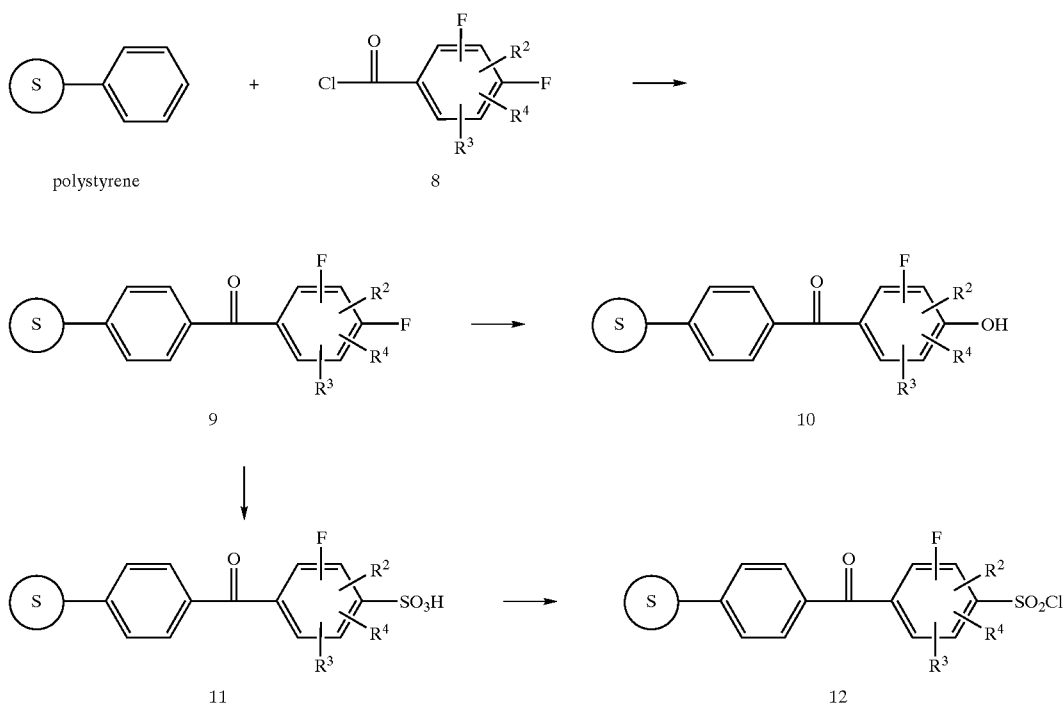

As shown in Scheme 3, Friedel-Crafts acylation of polystyrene with the 4-fluorobenzoyl chloride derivative 8, in the presence of a Lewis acid such as FeCl$_3$, SnCl$_4$ or AlCl$_3$, in a suitable organic solvent, provides the 4-fluorofluorobenzoyl resin compound 9. Reaction of 9 with hydroxide provides the 4-hydroxyfluorobenzoyl resin compound 10.

In a preferred aspect, polystyrene is acylated with the 4-fluorobenzoyl chloride derivative 8 in the presence of AlCl$_3$ in nitrobenzene to provide the 4-fluorobenzoyl resin compound 9. A mixture of 9 in water/cyclohexane is treated with sodium hydroxide and tetrabutylammonium hydrogen sulfate according to the procedure of Feldman et al., *J. Org. Chem.*, 56 (26), 7350–7354 (1991), to provide the 4-hydroxyfluorobenzoyl resin compound 10.

Reaction of the 4-hydroxyfluorobenzoyl resin compound 10 with an SO$_3^-$ equivalent such as potassium metabisulfite, in the presence of base in a suitable organic solvent such as dichloromethane, dichloroethane or chloroform, provides the fluorobenzoyl-4-sulfonic acid resin compound 11. Representative bases include diisopropylethylamine, pyridine, triethylamine, N-methylpiperidine, and the like. Reaction of the fluorobenzoyl-4-sulfonic acid resin compound 11 with an acid chloride such as chlorosulfonic acid, thionyl chloride, oxalyl chloride, and the like, in an inert organic solvent provides the fluorobenzoyl-4-sulfonyl chloride acid resin compound 12.

The preparation of the solid-phase reaction component of formula

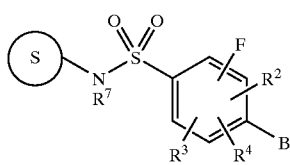
(14, 16)

wherein B is F or OH is outlined in Scheme 4.

Scheme 4

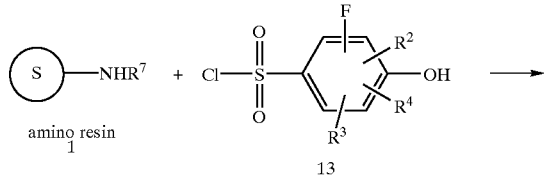

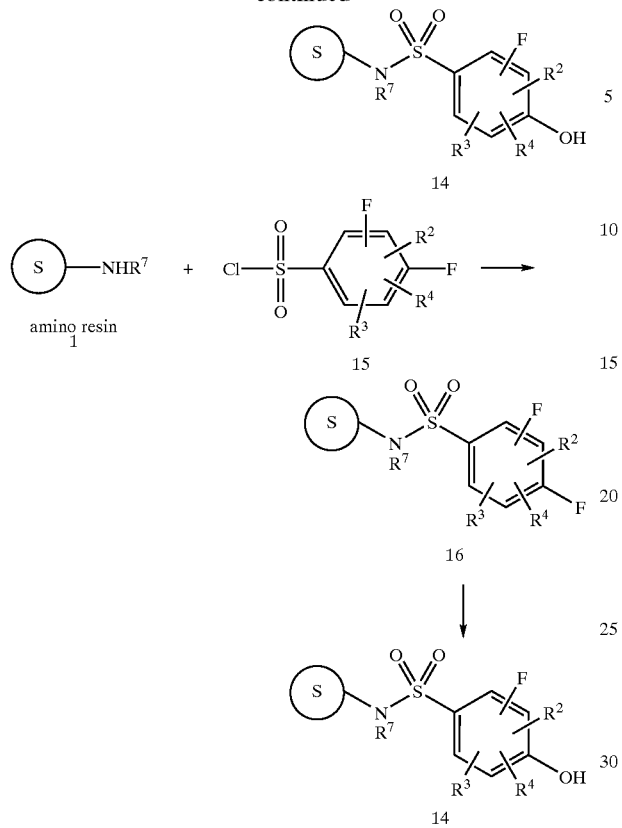

As shown in Scheme 4, reaction of amino resin 1 with the 4-hydroxyfluorophenylsulfonyl chloride compound 13 in the presence of a base, such as N-methylmorpholine, pyridine, collidine, triethylamine or diisopropylethylamine, in a suitable organic solvent, such as dichloromethane, dichloroethane, dioxane, THF or DMF, provides the 4-hydroxyfluorophenylsulfonamide resin compound 14. The reaction is preferably conducted in dichloromethane in the presence of collidine.

Alternatively, amino resin 1 is reacted with the 4-fluorofluorophenylsulfonyl chloride compound 15 as described above to give the 4-fluorofluorophenylsulfonamide resin compound 16, which is converted to the desired 4-hydroxyfluorophenylsulfonamide resin compound 14 under reaction conditions analogous to those described in Scheme 3 above.

The preparation of a solid-phase reaction component of formula

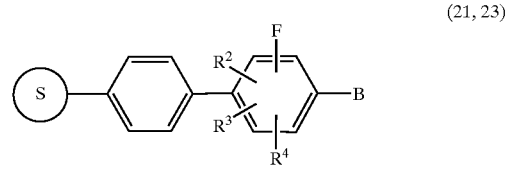

(21, 23)

wherein B is F, OH, SO$_3$H or SO$_2$Cl is shown in Scheme 5.

Scheme 5

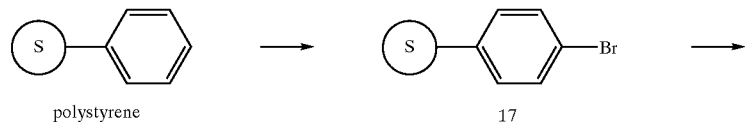

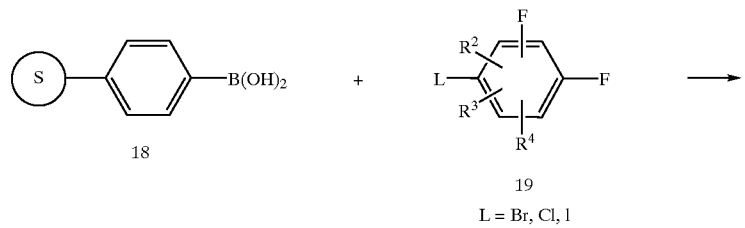

L = Br, Cl, I

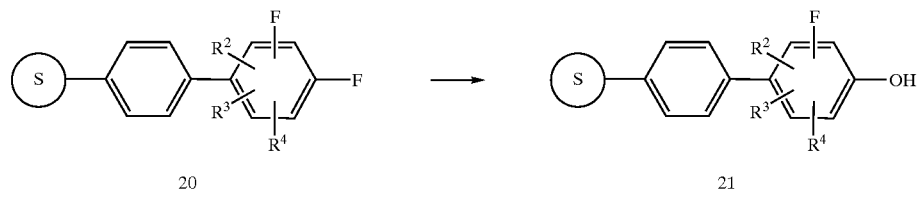

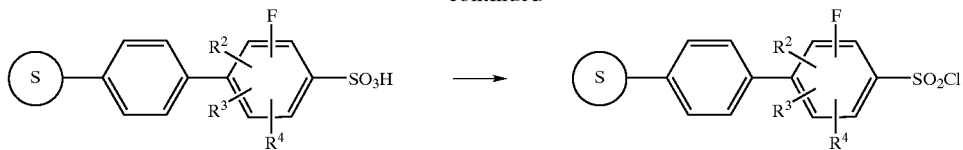

22 → 23

As shown in Scheme 5, bromination of polystyrene, for example using Br$_2$ in the presence of FeCl$_3$, Tl(OAc)$_3$ or BF$_3$ gives the brominated polystyrene resin compound 17. Metal halogen exchange, for example using an alkyllithium reagent such as n-butyllithium in benzene or TMEDA; addition of trimethylborate; and acidic workup provides the polystyryl boronic acid resin compound 18. Coupling of compound 18 with the fluorophenyl halide compound 19 using Suzuki conditions (catalytic Pd(0), basic conditions (see Frenette et al., *Tetrahedron Lett.*, 1994, 35, 9177 and Brown et al., *J. Amer. Chem. Soc.*, 1996, 118, 6331), provides the 4-fluorofluorophenyl polystyrene resin compound 20. Conversion of 20 to the 4-hydroxyfluorophenyl polystyrene resin compound 21, fluorophenyl-4-sulfonic acid polystyrene resin compound 22 or the fluorophenyl-4-sulfonyl chloride polystyrene resin compound 23 is accomplished under reaction conditions analogous to those described Scheme 3 above.

The preparation of a solid-phase reaction component of formula (27)

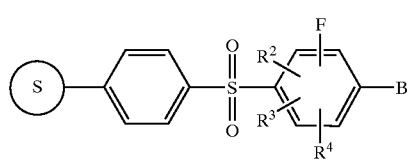

wherein B is F or OH is outlined in Scheme 6.

Scheme 6

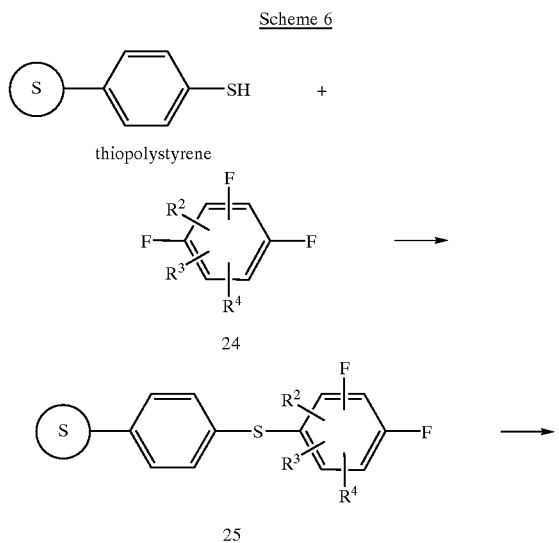

As shown in the foregoing Scheme 6, reaction of thiopolystyrene with a trifluorophenylbenzene compound 24 results in formation of the difluorophenylthio-polystyrene resin compound 25. The reaction is preferably carried out in a suitable solvent such as toluene, dioxane, DMF or DMSO, in the presence of base, preferably catalytic pyridine or N-methylmorpholine. Conversion of compound 25 to the 4-hydroxyfluorophenylthio-polystyrene resin compound 26 is accomplished as described in Scheme 3 above. Oxidation of compound 26, for example using m-chloroperbenzoic acid (MCPBA), provides the 4-hydroxyfluorophenylsulfonyl-polystyrene resin 27.

The preparation of the solid-phase reaction component of formula (31)

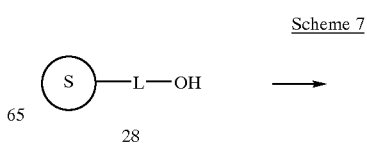

wherein (S),

L and P are as defined herein, is shown in Scheme 7.

Scheme 7

(S)—L—OH →

28

31

-continued

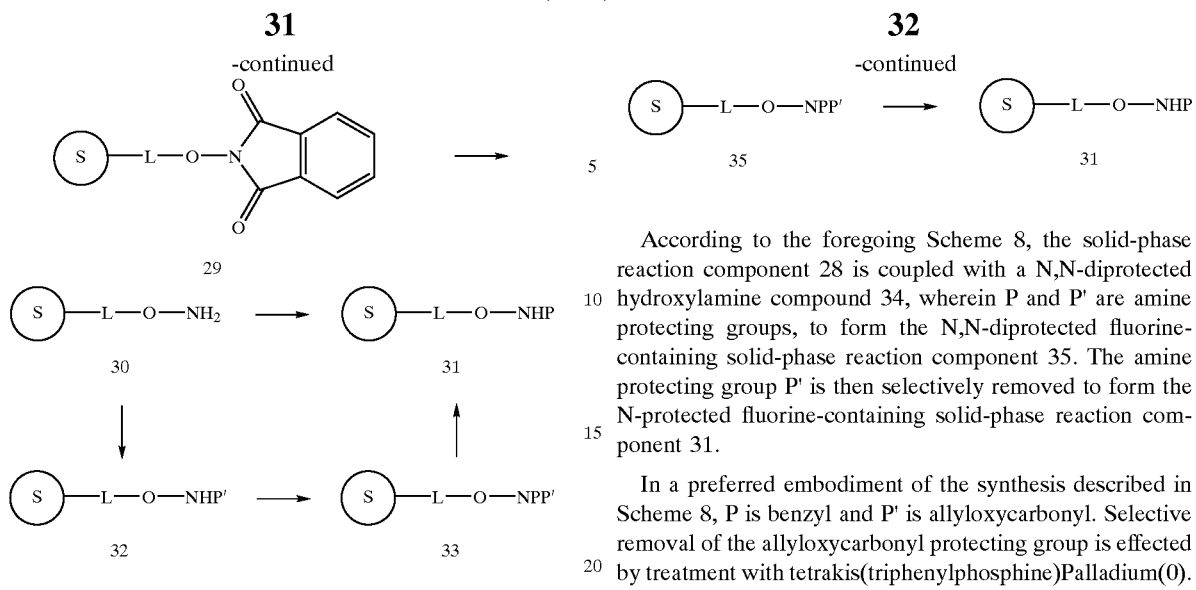

According to the foregoing Scheme 7, a polymeric hydroxy resin compound 28 is converted to the polymeric N-oxyphthalimido resin compound 29 by coupling with N-hydroxyphthalimide under Mitsunobu conditions (Mitsunobu, O., *Synthesis* 1981, 1); by conversion of the hydroxy group to a leaving group such as the mesylate followed by nucleophilic displacement with N-hydroxyphthalimide; or by reaction of the polymeric hydroxy resin compound with N-hydroxyphthalimide in the presence of an acid such as benzenesulfonic acid. Removal of the phthalimido group using techniques commonly known in the art such as treatment of 29 with hydrazine, or preferably methylamine, provides the fluorine-containing solid-phase reaction component 30 (in which P is H).

For example, coupling of 28 with N-hydroxyphthalimide is accomplished in the presence of diisopropylazodicarboxylate and triphenylphosphine in DMF. The phthalimido protection is then removed by methylaminolysis in THF at about 40° C.

Introduction of an amine protecting group, such as benzyl, using reagents and reaction conditions commonly known in the art, provides the fluorine-containing solid-phase reaction component 31 in which P is an amine protecting group.

In certain instances, the attempted introduction of certain amine protecting groups to the fluorine-containing solid-phase reaction component 30 results in diprotection of the N atom. Diprotection is preferably avoided by selective mono-protection of 30 with a protecting group P', to form the mono-N-protected fluorine-containing solid-phase reaction component 32, which is followed by introduction of the protecting group P to form the N,N-diprotected fluorine-containing solid-phase reaction component 33 and selective removal of P'. A preferred protecting group P' is allyloxycarbonyl, which is selectively cleaved in the presence of additional amine protecting groups by Pd(0).

An alternative route to the solid-phase reaction component 31 is outlined in Scheme 8.

Scheme 8

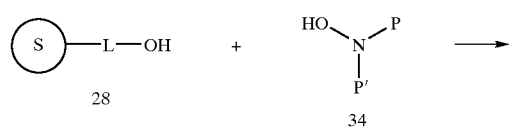

32

-continued

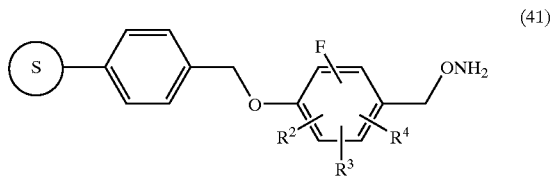

According to the foregoing Scheme 8, the solid-phase reaction component 28 is coupled with a N,N-diprotected hydroxylamine compound 34, wherein P and P' are amine protecting groups, to form the N,N-diprotected fluorine-containing solid-phase reaction component 35. The amine protecting group P' is then selectively removed to form the N-protected fluorine-containing solid-phase reaction component 31.

In a preferred embodiment of the synthesis described in Scheme 8, P is benzyl and P' is allyloxycarbonyl. Selective removal of the allyloxycarbonyl protecting group is effected by treatment with tetrakis(triphenylphosphine)Palladium(0).

The N,N-diprotected hydroxylamine compound 34 is prepared by sequential introduction of the protecting groups P and P' to an O-protected hydroxylamine compound of formula $H_2NOP^2$ wherein $P^2$ is a hydroxy protecting group. A preferred hydroxy protecting group is alkyl The amine protecting groups P and P' are then introduced using reagents and reaction conditions well known in the art of organic synthesis. For Example, reaction of O-tert-butylhydroxylamine with allyloxychloroformate results in formation of N-allyloxycarbonyl-O-tert-butylhydroxylamine, which is then reacted with benzyl bromide to form N-benzyl-N-allyloxycarbonyl-O-tert-butylhydroxylamine. Treatment of N-benzyl-N-allyloxycarbonyl-O-tert-butylhydroxylamine with trifluoroacetic acid gives N-benzyl-N-allyloxycarbonylhydroxylamine.

The preparation of a solid-phase reaction component of formula (41)

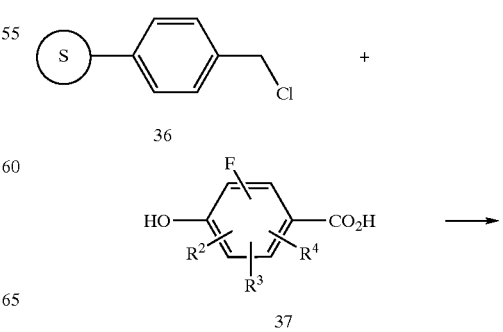

is shown in Scheme 9.

Scheme 9

-continued

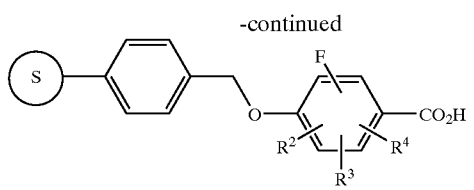

38

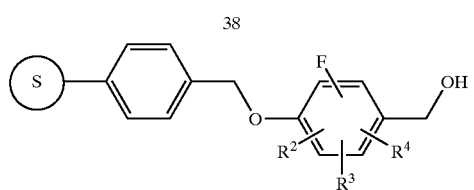

39

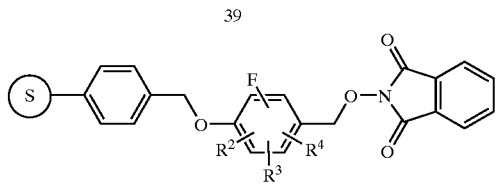

40

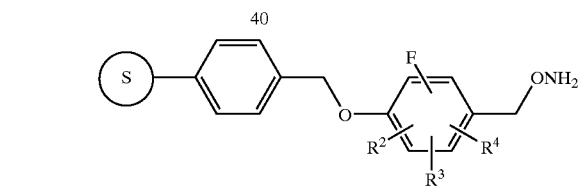

41

According to the foregoing Scheme 9, a polymeric chloromethyl resin compound such as chloromethyl polystyrene (36, Merrifield resin) is reacted with 4-hydroxyfluorobenzoic acid compound 37 in the presence of base to form the 4-carboxyfluorophenoxymethyl resin compound 38. Reduction of the carboxylic acid group, for example using $LiAlH_4$, diisobutylaluminum hydride, or $BH_3$-THF, provides the 4-hydroxymethylfluorophenoxymethyl resin compound 39. Conversion of 39 to the hydroxyphthalimido resin compound 40 followed by removal of the phthalimido group as described in Scheme 7 above, provides the fluorine-containing solid-phase reaction component 41.

The preparation of a solid-phase reaction compound of formula (46)

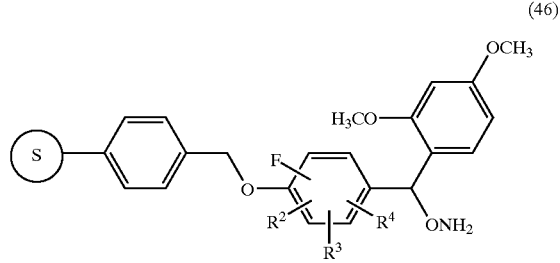

is shown in Scheme 10.

Scheme 10

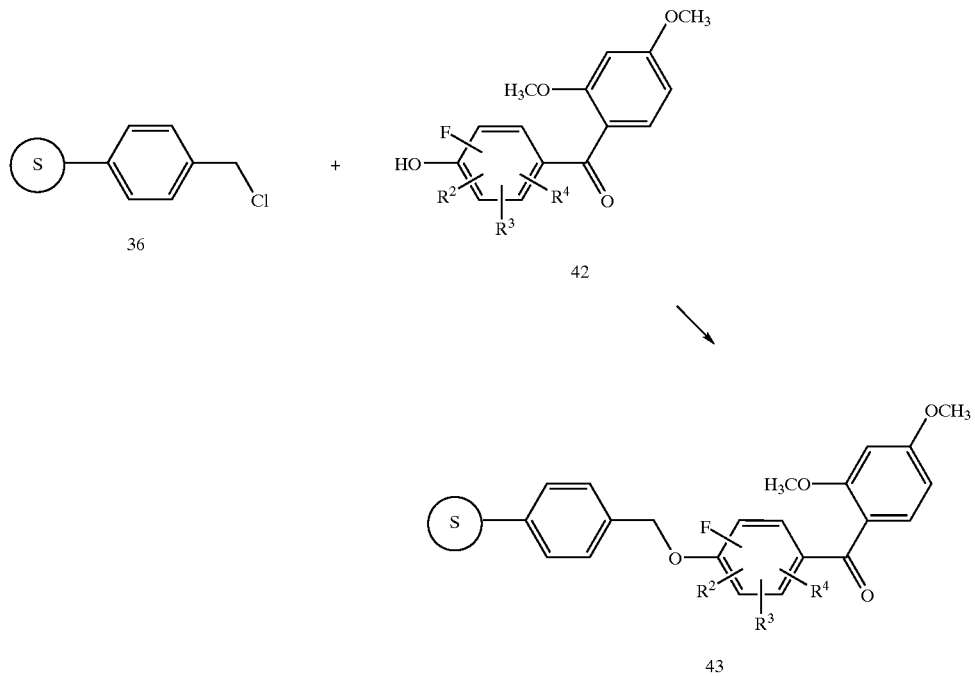

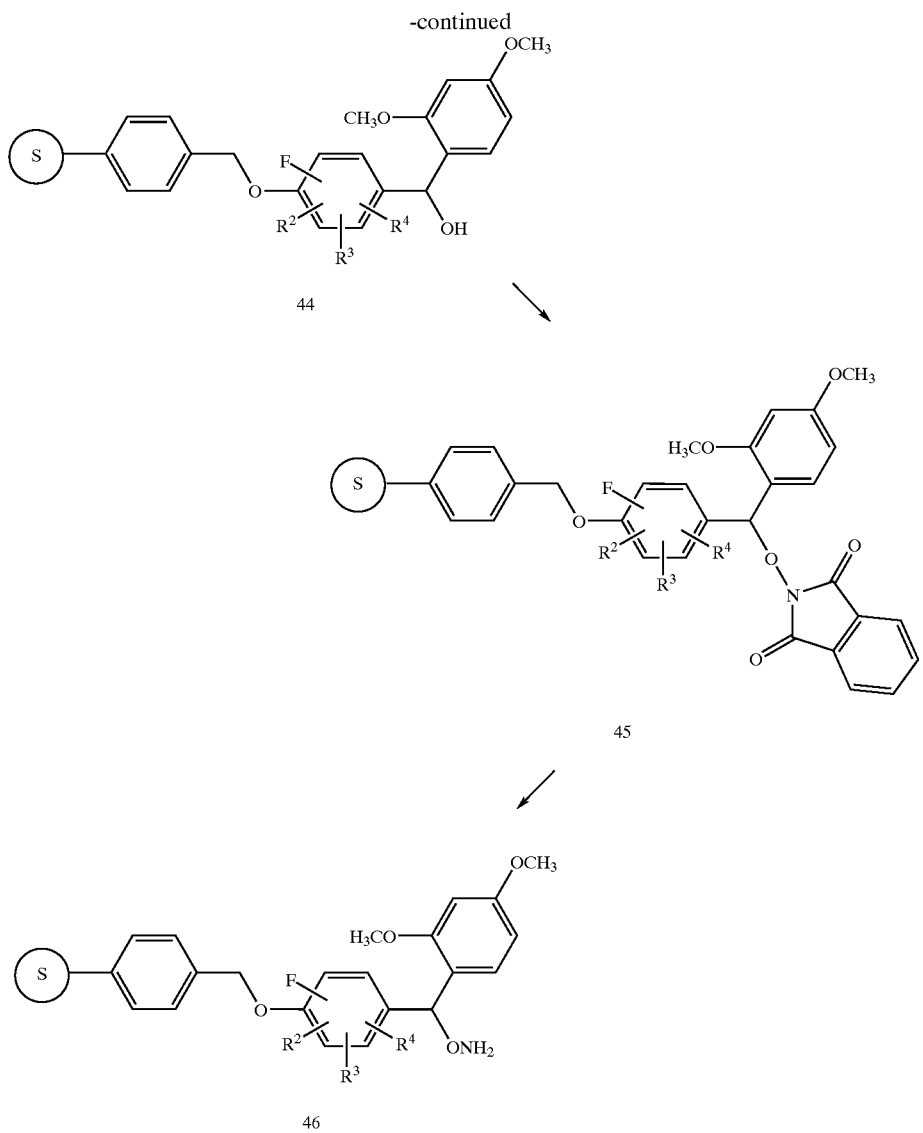

According to the foregoing Scheme 10, a polymeric chloromethyl resin compound 36 is reacted with a ketone 42 in the presence of base as described in Scheme 9 above to form the 4-(2',4'-dimethoxyphenylcarbonyl)-fluorophenoxymethyl-resin compound 43. Reduction of the carbonyl, for example using LiBH$_4$, provides the 4-(hydroxymethyl-2,4'-dimethoxyphenyl)-fluorophenoxymethyl resin compound 44. Conversion of 44 to the hydroxyphthalimido resin compound 45, followed by removal of the phthalimido group as described in Scheme 7 above, provides the solid-phase reaction component 46.

Still more preferred solid-phase reaction components for use according to the method of this invention have formula IV wherein $R^1$, $R^2$, $R^3$ and $R^4$ are F; and one of $R^5$ and $R^6$ is H and the other of $R^5$ and $R^6$ is H or 2,4-dimethoxyphenyl.

Other still more preferred solid-phase reaction components for use according to the method of this invention have formula IV wherein $R^1$, $R^2$, $R^3$ and $R^4$ are F; and one of $R^5$ and $R^6$ is H and the other of $R^5$ and $R^6$ is H or 2,4-dimethoxyphenyl; and B is F, OW or SO$_2$Z.

Other still more preferred solid-phase reaction components for use according to the method of this invention have formula IV wherein $R^1$, $R^2$, $R^3$ and $R^4$ are F; and one of $R^5$ and $R^6$ is H and the other of $R^5$ and $R^6$ is H or 2,4-dimethoxyphenyl; B is F, OW or SO$_2$Z; and A is phenylene, —C(O)—, —YC(O)—, —SO$_2$—, —NR$^7$SO$_2$— or —CHR$^7$O—.

Representative still more preferred solid-phase reaction components include, but are not limited to:

4-carboxy-2,3,5,6-tetrafluorophenoxymethyl-copoly (styrene-1% divinylbenzene) resin, designated herein as

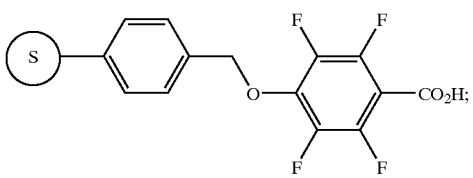

4-(O-methylhydroxylamine)-2,3,5,6-tetrafluorophenoxymethyl-copoly(styrene-1% divinylbenzene) resin, designated herein as

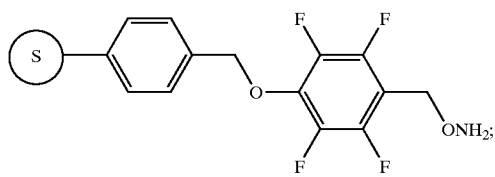

4-(2',4'-dimethoxyphenyl-O-methylhydroxylamine)-2,3,5,6-tetrafluorophenoxymethyl-copoly(styrene-1% divinylbenzene) resin, designated herein as

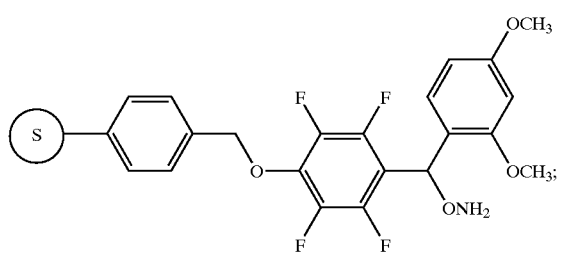

4-hydroxy-2,3,5,6-tetrafluorobenzamidomethyl-polystyrene resin, designated herein as

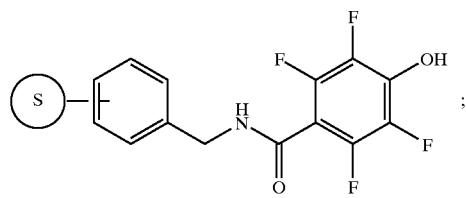

4-(N,N'-didisopropyl-isourea)-2,3,5,6-tetrafluorotetrafluorobenzamidomethyl-copoly(styrene-1%-divinylbenzene)-resin, designated herein as

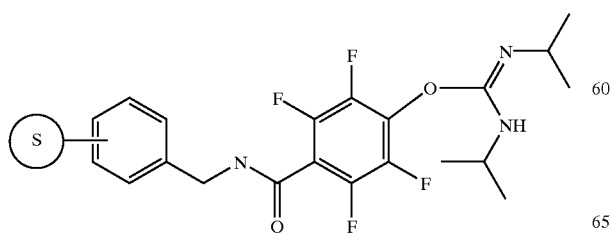

4-(tripyrolidinium-O-phosphonium)-2,3,5,6-tetrafluorotetrafluorobenzamidomethyl-copoly(styrene-1%-divinylbenzene)-resin, designated herein as

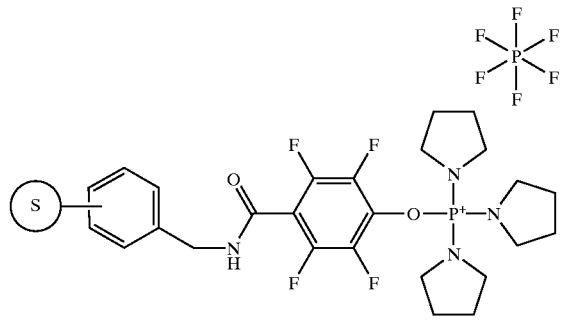

2,3,5,6-tetrafluorobenzamidomethyl-4-sulfonic acid-polystyrene resin, designated herein as

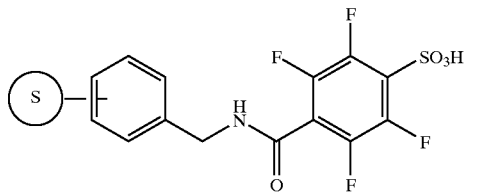

2,3,5,6-tetrafluorobenzamidomethyl-4-sulfonyl chloride-polystyrene resin, designated herein as

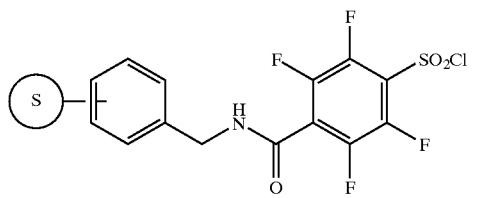

4-hydroxy-2,3,5,6-tetrafluorobenzoyloxymethyl-polystyrene resin, designated herein as

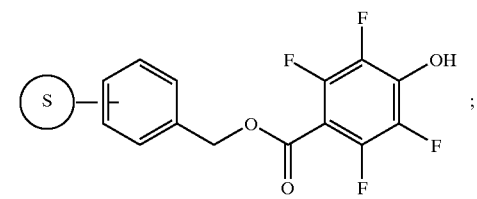

2,3,5,6-tetrafluorobenzoyloxymethyl-4-sulfonic acid-polystyrene resin, designated herein as

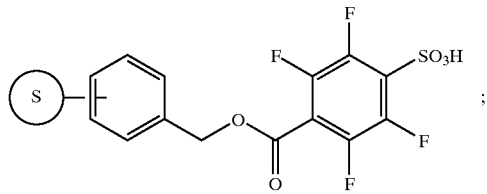

2,3,5,6-tetrafluorobenzoyloxymethyl-4-sulfonyl chloride-polystyrene resin, designated herein as

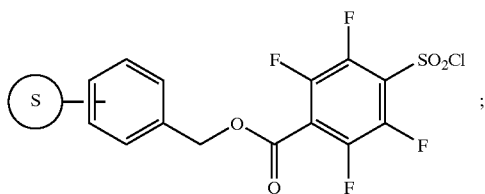

4-hydroxy-2,3,5,6-tetrafluorobenzoyl-polystyrene resin, designated herein as

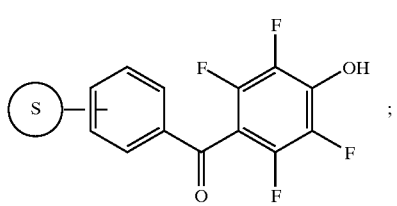

2,3,5,6-tetrafluorobenzoyl-4-sulfonic acid-polystyrene resin, designated herein as

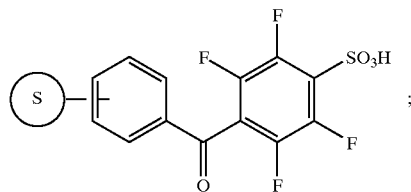

2,3,5,6-tetrafluorobenzoyl-4-sulfonyl chloride-polystyrene resin, designated herein as

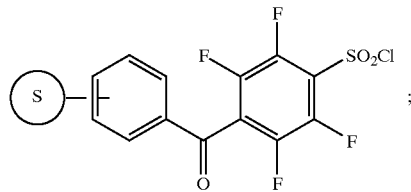

4-hydroxy-2,3,5,6-tetrafluorophenylsulfonamidomethyl-polystyrene resin, designated herein as

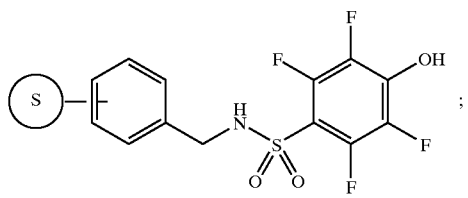

2,3,5,6-tetrafluorophenylsulfonamidomethyl-4-sulfonic acid-polystyrene resin, designated herein as

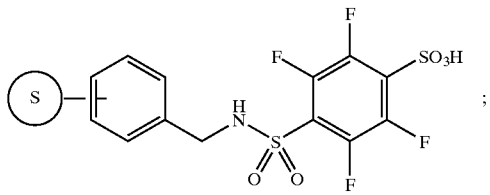

2,3,5,6-tetrafluorophenylsulfonamidomethyl-4-sulfonyl chloride-polystyrene resin, designated herein as

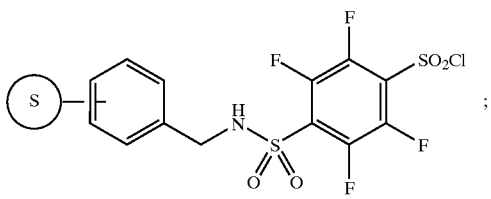

N-(4-hydroxy-2,3,5,6-tetrafluorobenzoyl)-piperidinomethyl-polystyrene resin, designated herein as

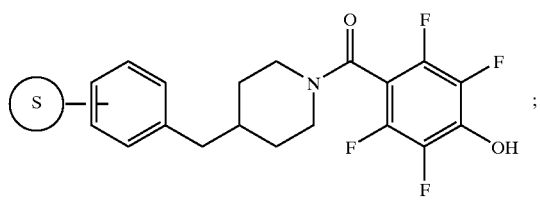

N-(2,3,5,6-tetrafluorobenzoyl-4-sulfonic acid)-piperidinomethyl-polystyrene resin, designated herein as

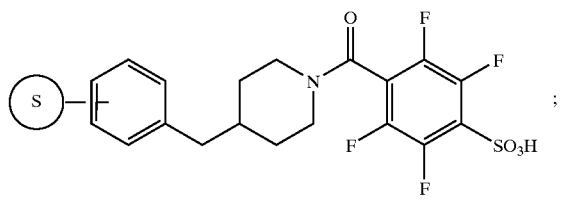

N-(2,3,5,6-tetrafluorobenzoyl-4-sulfonyl chloride)-piperidinomethyl-4-polystyrene resin, designated herein as

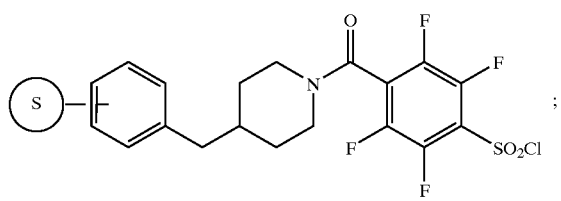

N-(4-hydroxy-2,3,5,6-tetrafluorophenylsulfonyl)-piperidinomethyl-polystyrene resin, designated herein as

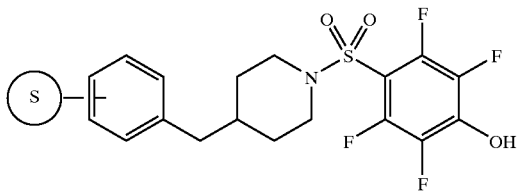

N-((2,3,5,6-tetrafluorophenyl-4-sulfonic acid)sulfonyl)-piperidinomethyl-polystyrene resin, designated herein as

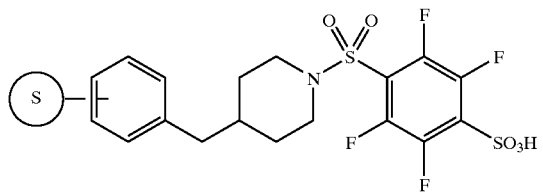

N-((2,3,5,6-tetrafluorophenyl-4-sulfonyl chloride)sulfonyl)-piperidinomethyl-polystyrene resin, designated herein as

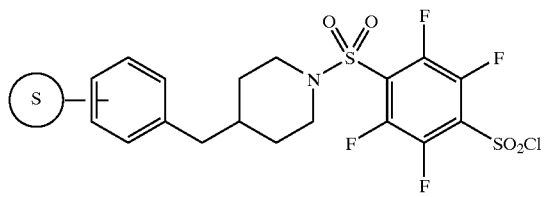

4-hydroxy-2,3,5,6-tetrafluorophenyl-polystyrene resin, designated herein as

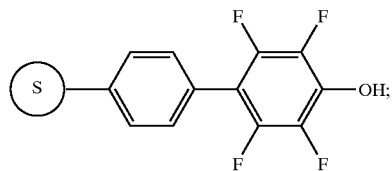

2,3,5,6-tetrafluorophenyl-4-sulfonic acid-polystyrene resin, designated herein as

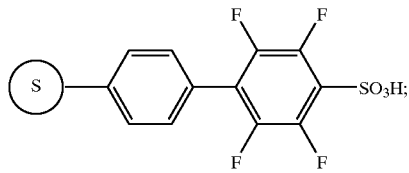

2,3,5,6-tetrafluorophenyl-4-sulfonyl chloride polystyrene resin, designated herein as

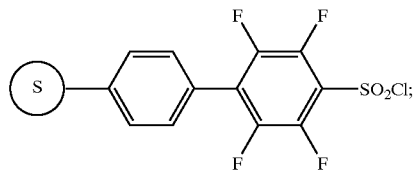

4-hydroxy-2,3,5,6-tetrafluorophenylsulfonyl-polystyrene resin, designated herein as

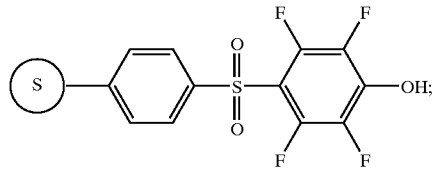

2,3,5,6-tetrafluorophenylsulfonyl-4-sulfonic acid-polystyrene resin, designated herein as

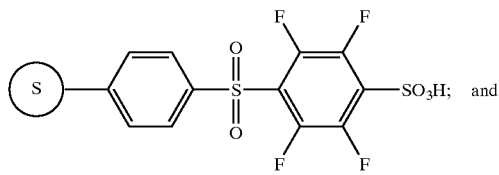

2,3,5,6-tetrafluorophenylsulfonyl-4-sulfonyl chloride-polystyrene resin, designated herein as

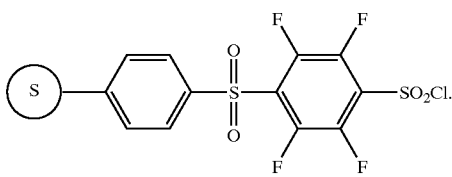

Still more preferred solid-phase reaction components for use according to the method of this invention have formula IV wherein $R^1$, $R^2$, $R^3$ and $R^4$ are F; one of $R^5$ and $R^6$ is H and the other of $R^5$ $R^6$ is 2,4-dimethoxyphenyl; and A is phenylene, —C(O)—, —YC(O)—, —SO$_2$—, —NR$^7$SO$_2$— or —CHR$^7$O—.

Representative more preferred solid-phase reaction components include:
  4-carboxy-2,3,5,6-tetrafluorophenoxymethyl-copoly (styrene-1% divinylbenzene) resin,
  4-(O-methylhydroxylamine)-2,3,5,6-tetrafluorophenoxymethyl-copoly(styrene-1% divinylbenzene) resin,
  4-(2',4'-dimethoxyphenyl-O-methylhydroxylamine)-2,3,5,6-tetrafluorophenoxymethyl-copoly(styrene-1% divinylbenzene) resin,
  4-hydroxy-2,3,5,6-tetrafluorobenzamidomethyl-polystyrene resin,
  4-(N,N'-didisopropyl-isourea)-2,3,5,6-tetrafluorotetrafluorobenzamidomethyl-copoly(styrene-1%-divinylbenzene)-resin,
  4-(tripyrolidinium-O-phosphonium)-2,3,5,6-tetrafluorotetrafluorobenzamidomethyl-copoly(styrene-1%-divinylbenzene)-resin, 2,3,5,6-tetrafluorobenzamidomethyl-4-sulfonic acid-polystyrene resin,
2,3,5,6-tetrafluorobenzamidomethyl-4-sulfonyl chloride-polystyrene resin,
4-hydroxy-2,3,5,6-pentafluorobenzoyl-polystyrene resin,
2,3,5,6-tetrafluorobenzoyl-4-sulfonic acid-polystyrene resin,
2,3,5,6-tetrafluorobenzoyl-4-sulfonyl chloride-polystyrene resin,
4-hydroxy-2,3,5,6-tetrafluorophenylsulfonamidomethyl-polystyrene resin,
2,3,5,6-tetrafluorophenylsulfonamidomethyl-4-sulfonic acid-polystyrene resin and
2,3,5,6-tetrafluorophenylsulfonamidomethyl-4-sulfonyl chloride-polystyrene resin.

An especially preferred solid-phase reaction component is 4-hydroxy-2,3,5,6-tetrafluorobenzamidomethyl-polystyrene resin.

The use of $^{19}$F NMR to quantify and monitor the preparation of fluorine-containing activated ester solid-phase reaction product of formula

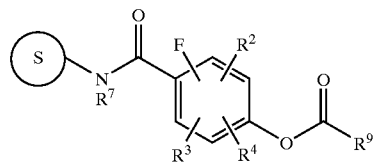

(36)

is shown in Scheme 11.

Scheme 11

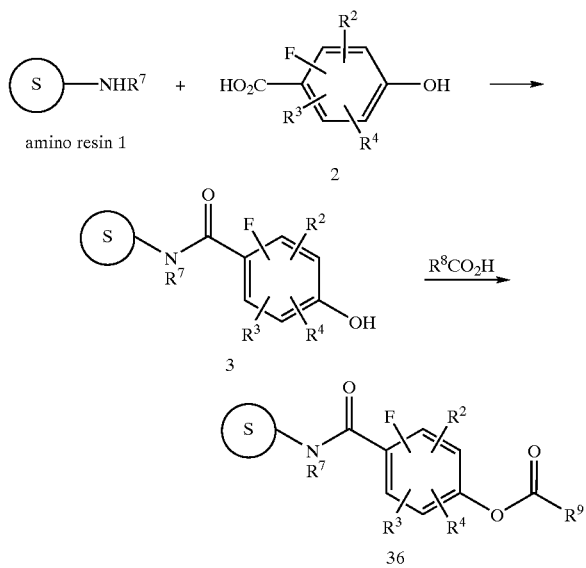

As shown in the foregoing scheme 11, the first step in the preparation of the fluorine-containing activated ester solid-phase reaction component consists of loading amino resin 1 with the 4-hydroxyfluorobenzoic acid derivative 2 as described in Scheme I above. The level of resin loading to the amino resin 1 is determined as described above.

The second step in the preparation of the fluorine-containing activated ester solid-phase reaction component 36 is coupling of the 4-hydroxy fluorine-containing solid-phase reaction component 3 with a carboxylic acid compound of formula $R^9CO_2H$. Coupling times range from about 2 to about 24 hours, depending on the nature of the 4-hydroxy fluorine-containing solid-phase reaction component 3, the carboxylic acid compound $R^9CO_2H$, solvent, reaction temperature and activating agent. Coupling is preferably accomplished using diisopropylcarbodiimide (DIC) in the presence of catalytic 4-dimethylaminopyridine (DMAP), or bromotripyrrolidinophosphonium hexafluorophosphate (PyBroP™) in the presence of triethylamine (TEA). The coupling reaction being carried out in a suitable solvent such as benzene, dichloromethane, dichloroethane, dioxane, THF or DMF, at about ambient temperature over about 18 hours. A preferred solvent is anhydrous DMF. The fluorine-containing activated ester solid-phase reaction component 36 is then washed with a suitable organic solvent or solvents to remove excess reagents.

The coupling reaction described above results in downfield shift of the $^{19}$F resonances in the fluorine-containing activated ester solid-phase reaction component 36 relative to the 4-hydroxy fluorine-containing activated ester solid-phase reaction component 3. Consequently, loading of the carboxylic acid compound $R^9CO_2H$ can be determined by comparison of relative integral values of the $^{19}$F resonances corresponding to the activated ester and phenol moieties. These measurements are independent of resin quantity and total sample volume.

In a similar fashion, subsequent reactions performed on the fluorine-containing activated ester solid-phase reaction component 36 can be quantifed using the techniques described above. For example, the fluorine-containing activated ester solid-phase reaction component 36 can be cleaved with an amine of formula $HNR^{24}R^{25}$, wherein $R^{24}$ and $R^{25}$ are H, aliphatic or aromatic, to form an amide of formula 37 with concomitant regeneration of the 4-hydroxy fluorine-containing activated ester solid-phase reaction component 3 as shown in Scheme 12.

Scheme 12

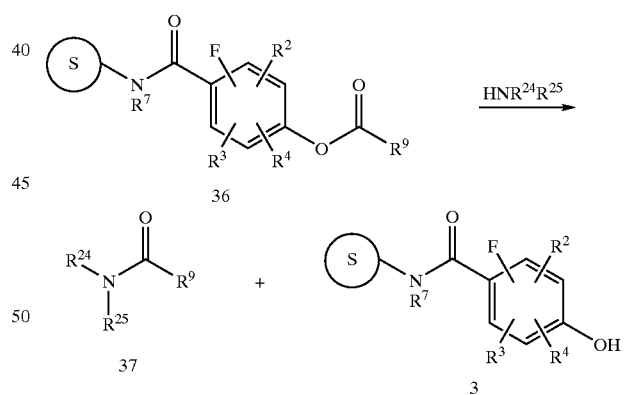

The reaction described in Scheme 12 above is quantified by comparison of relative integral values of the $^{19}$F resonances corresponding to fluorine-containing activated ester solid-phase reaction component 36 and 4-hydroxy fluorine-containing solid-phase reaction component 3.

In a similar fashion, the progress of a solid-phase reaction over time may be monitored by periodically obtaining a $^{19}$F NMR spectrum of the reaction mixture and monitoring the disappearance of the $^{19}$F resonances corresponding to the fluorine-containing solid-phase reaction component.

Solid-phase synthetic techniques are used extensively in the preparation of peptides. Peptide synthesis on solid supports generally involves building a peptide from the carboxyl or C-terminal end in which the C-terminal amino acid, with its α-amino group protected, is attached to a solid-phase polymer.

The N-protecting group is then cleaved off, and the next amino acid, also N-protected, is coupled by a peptide bond to the α-amino group of the amino acid attached to the solid support as described above. The cycle of deprotection of the prior amino acid and coupling the additional amino acid is repeated until the peptide is completed. Any reactive side chains of the amino acids are protected by chemical groups that can withstand the coupling and N$^\alpha$-deprotection procedure but can be removed at the end of the synthesis.

The yields of any of the coupling reactions utilized in the peptide synthesis described above have heretofore been determined by cleaving a sample of the peptide from the resin, purifying the peptide and calculating the yield. By using the $^{19}$F NMR methodology described herein, the yield is determined simply by comparing the $^{19}$F resonances of the starting and product resin-bound peptide at each step of the synthesis.

It is to be understood that this invention covers all appropriate combinations of the particular and preferred groupings referred to herein.

The foregoing may be better understood by reference to the following examples, which are presented for illustration and are not intended to limit the scope of this invention.

Fluorine NMR

Unless otherwise indicated, $^{19}$F NMR experiments are carried out on a Varian Unityplus (or Inova) spectrometer operating at a $^{19}$F frequency of 470.228 MHz. The $^1$H Nanoprobe is tuned to $^{19}$F frequency. Typically, spectra are acquired with a (delay-pulse-acquire) sequence repeated for nt number of transients. Typical spectral width is 100,000 Hz and the chemical shifts are referenced relative to CFCl$_3$ using the transmitter frequency. The magic angle spectra are acquired using a Nanoprobe in which the sample is oriented at a magic angle (54.7 degrees) relative to the magnetic field and the sample is spun at a rate of about 1000 to about 2000 Hz. For quantitative analyses employing an external standard, the samples are prepared by swelling an accurately weighed 2–3 mg sample of fluorine-containing solid-phase reaction product with about 40 μL of deuterated N,N-dimethylformamide. The external standard is typically added first to the dry fluorine-containing solid-phase reaction product in the sample tube. The external standard is preferably 3-fluorobenzamide, in which case, 20 μL of a 0.125 M solution of 3-fluorobenzamide in deuterated DMF is added to the dry resin in the sample tube.

Figure 7:
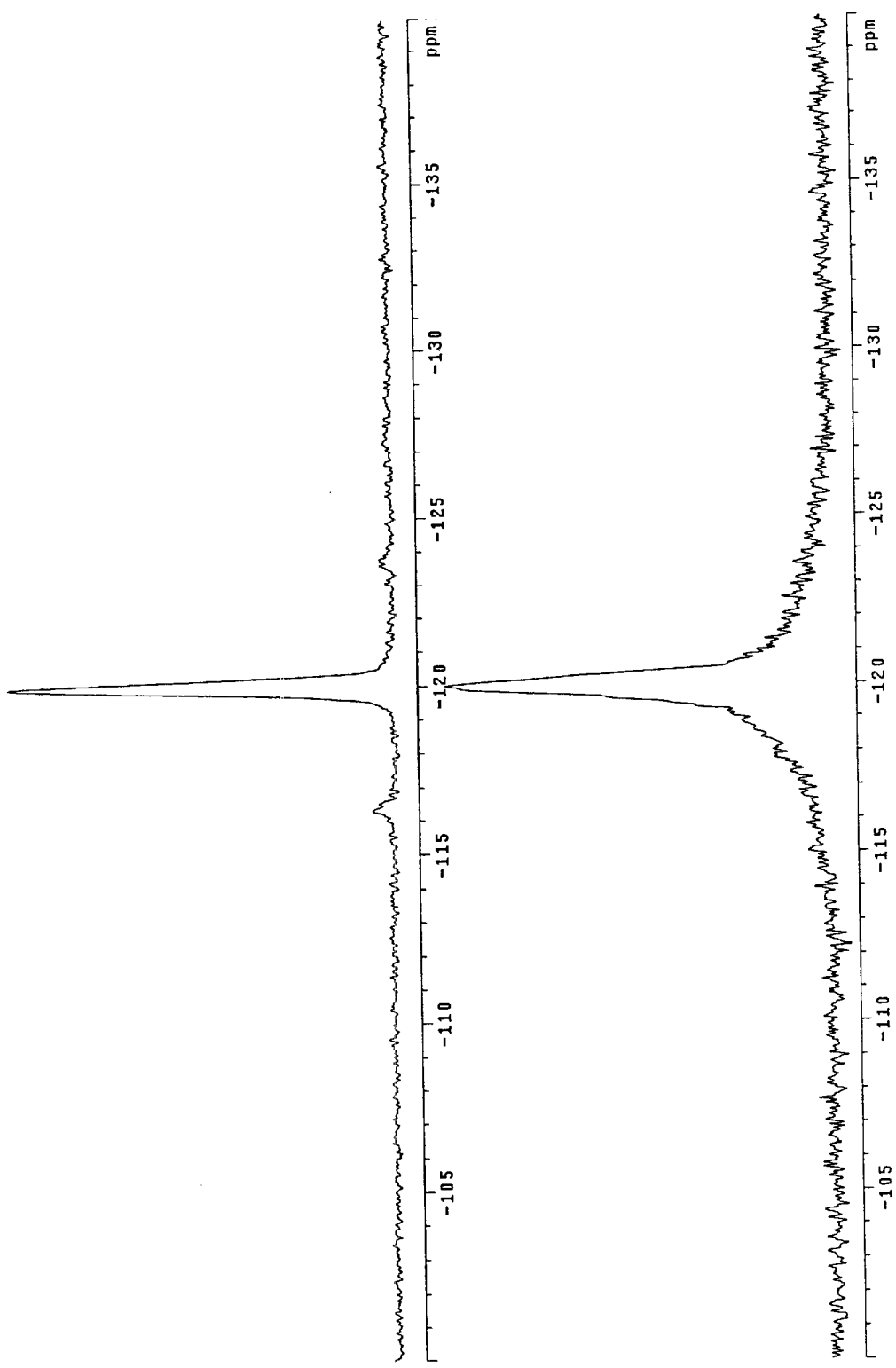
FIG. 7 shows $^{19}$F NMR spectra under MAS (upper trace) and standard 5 mm sample tube (lower trace) conditions for copoly(styrene-4-fluorostyrene-4-chloromethylstyrene-1%-divinylbenzene)resin in CDCl$_3$ solvent.
Figure 9:
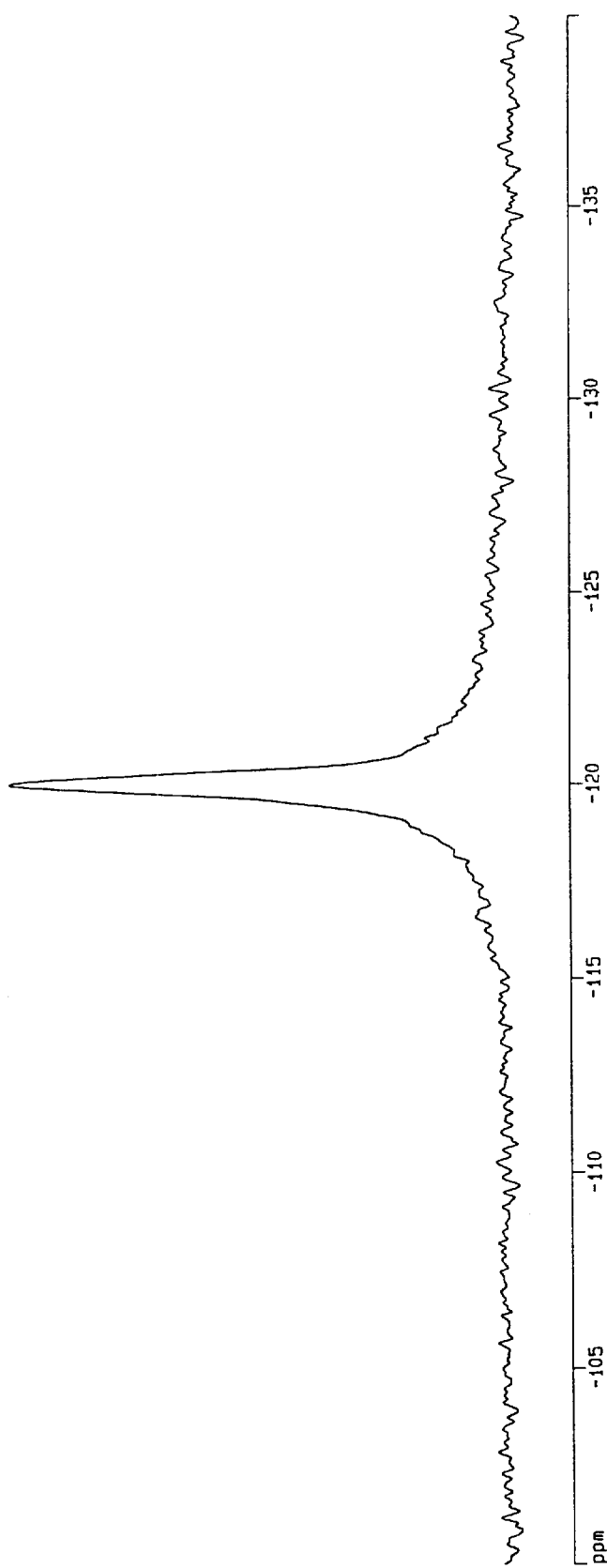
FIG. 9 is the $^{19}$F NMR spectrum of copoly(styrene-4-fluorostyrene-4-chloromethylstyrene-1%-divinylbenzene)-resin (approximately 0.40 mmol F/g resin) in CDCl$_3$ acquired on a 300 MHz spectrometer using a standard 5 mm sample tube. The spectral acquisition time was 3.57 minutes.

Gel-phase $^{19}$F NMR experiments are also performed in standard 5 mm diameter sample tubes. Acquired using equivalent acquisition parameters (e.g. number of transients=16), the spectra depicted in FIG. 7 demonstrate that $^{19}$F NMR linewidths are slightly decreased by magic angle spinning. In addition, these experiments have been carried out at 200, 300 and 500 MHz ($^1$H) field strengths. FIG. 9 shows the $^{19}$F NMR spectrum of copoly(styrene-4-fluorostyrene-4-chloromethylstyrene-1%-divinylbenzene)-resin acquired in CDCl$_3$ using a standard 5 mm sample tube in a 300 MHz spectrometer. The use of standard 5 mm tubes permits rapid automated spectral acquisition for high throughput analysis.

EXAMPLE 1

Preparation of 4-Hydroxy-2,3,5,6-tetrafluorobenzamidomethyl-copoly(styrene-1%-divinylbenzene)-resin

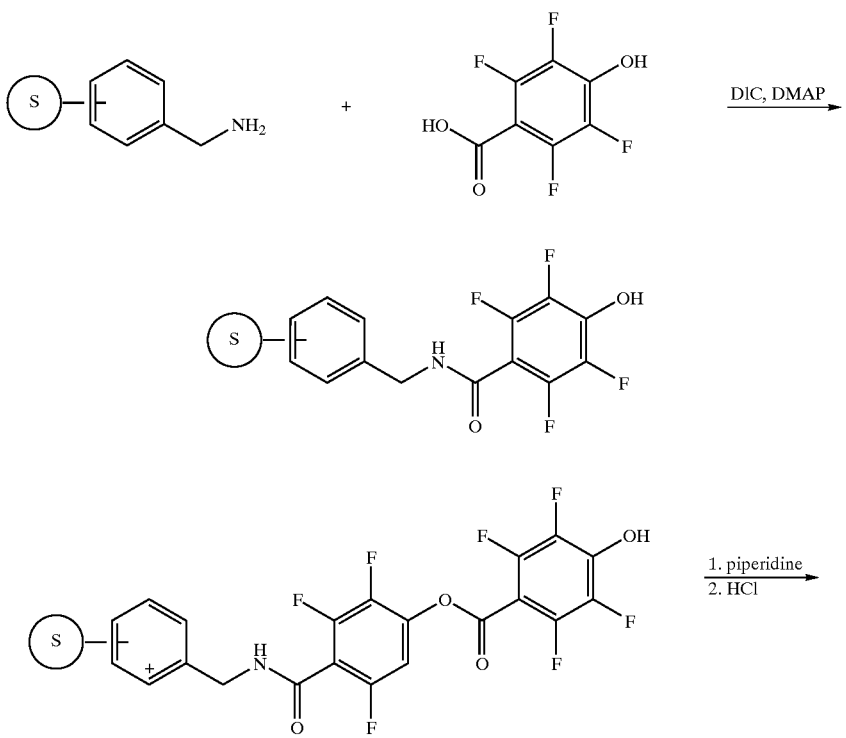

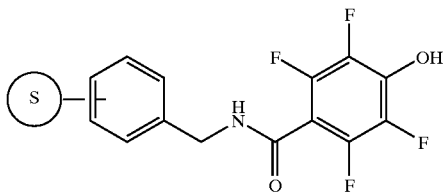

To a stirred slurry of aminomethyl polystyrene (0.82 mmol/g, 800 g, 656 mmol) in DMF (8 L) is added a solution of 2,3,5,6-tetrafluoro-4-hydroxybenzoic acid (234 g, 984 mmol) in DMF (1 L), a solution of 1-hydroxybenzotriazole (133 g, 984 mmol) in DMF (250 mL) and diisopropylcarbodiimide (124 g, 984 mmol), and the mixture is stirred overnight at ambient temperature. The reaction mixture is then filtered and the resin washed with DMF (1×1 L; 5×2 L), THF (3×2 L; 2×3 L) and $CH_2Cl_2$ (3×3 L). The resin is then air-dried in trays for 2 days to afford a resin product mixture containing the desired amide product and some ester by-product The resin product mixture (995 g) is then added to a mixture of piperidine (125 mL) and DMF (6 L). DMF (2 L) is added to facilitate stirring and the mixture is stirred for 1 hour. The mixture is then filtered and the resin is washed with DMF (10×500 ml) and dried in vacuo.

The resin is then suspended in DMF (4 L), and a solution of 2M HCl (750 mL) in DMF (2 L) is added, and the mixture is stirred for 0.5 hours. The resin is then filtered, washed with DMF (10 L) and THF (10 L) and dried overnight in vacuo at ambient temperature to afford the desired amide product.

EXAMPLE 2

Preparation of 2,3,4,5,6-Tetrafluorobenzoyl-copoly(styrene-1%-divinylbenzene)-resin

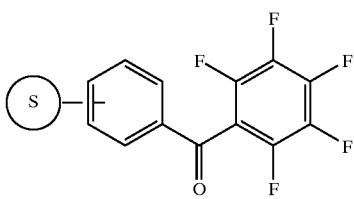

To a mixture of copoly(styrene-1%-divinylbenzene) resin (100–200 mesh, 10 g) and pentafluorobenzoyl chloride (25 g) in nitrobenzene (250 mL) is added $AlCl_3$ (1.0 M in nitrobenzene, 38 mL), and the reaction mixture is stirred at 60° C. for 18 hours. The reaction mixture is then poured into a mixture of DMF (30 mL), concentrated HCl (20 mL) and ice (80 g). The mixture is stirred for 30 minutes, filtered, and the resin is washed with 3:1 DMF-$H_2O$ until the washings are colorless. The resin is then washed with warm DMF and 2:1 dichloromethane-methanol (6×) and dried in vacuo. $^{19}F$ NMR δ −146.5 (2F), −157 (1F), −165.5 (2F).

EXAMPLE 3

Preparation of 4-Hydroxy-2,3,5,6-tetrafluorobenzoyl-copoly(styrene-1%-divinylbenzene)-resin

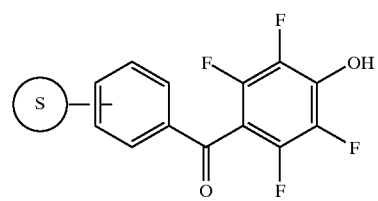

The title resin is prepared by treating a mixture of 2,3,4,5,6-pentafluorobenzoyl-copoly(styrene-1%-divinylbenzene)-resin in water/cyclohexane with sodium hydroxide and tetrabutylammonium hydrogen sulfate as described by Feldman et al., J. Org. Chem., 56 (26), 7350–7354 (1991).

EXAMPLE 4

Preparation of 2,3,5,6-Tetrafluorobenzoyl-4-sulfonic Acid-copoly(styrene-1%-divinylbenzene)-resin

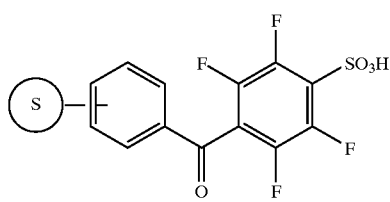

A mixture of 2,3,4,5,6-pentafluorobenzoyl-copoly(styrene-1%-divinylbenzene)-resin (325 mg), prepared as in Example 2, dichloromethane (3 mL), $H_2O$ (1 mL), triethylamine (1.2 mL) and potassium metabisulfite (560 mg) is stirred for 3 days. The resin is then washed with dichloromethane (6×) and dried in vacuo at 40° C. $^{19}F$ NMR δ −142 (2F), −147 (2F).

EXAMPLE 5

Preparation of 2,3,5,6-Tetrafluorobenzoyl-4-sulfonyl Chloride-copoly(styrene-1%-divinylbenzene)-resin

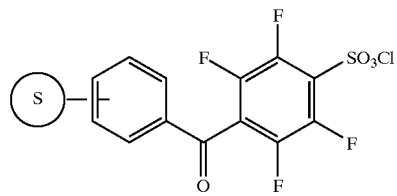

The 2,3,5,6-tetrafluorobenzene-4-sulfonic acid-copoly(styrene-1%-divinylbenzene)resin (300 mg), prepared in Example 4, is swelled in carbon tetrachloride (3 mL), and chlorosulfonic acid (1 mL) is added. The reaction mixture is stirred for 24 hours and then is quenched with acetic acid. The resin is filtered, washed with dichloromethane (6×) and ether (4×) and dried in vacuo at 40° C. $^{19}$F NMR δ –142 (2F), –146.5 (2F).

EXAMPLE 6

Preparation of 2,3,4,5,6-Pentafluorophenylsulfonamidomethyl-copoly(styrene-1%-divinylbenzene)resin

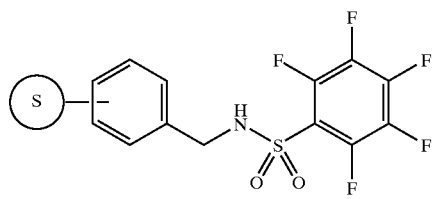

Aminomethyl polystyrene (1 g, 1.2 mmol) is swelled with dichloromethane and 2,4,6-collidine (0.475 mL, 3.6 mmol), and 2,3,4,5,6-pentafluorophenylsulfonyl chloride (1.44 mmol) are added. The reaction mixture is stirred for 5 hours and the resin is filtered, washed with dichloromethane (6×) and dried in vacuo at 40° C.

EXAMPLE 7

Preparation of 4-Hydroxy-2,3,5,6-tetrafluorophenylsulfonamidomethyl-copoly(styrene-1%-divinylbenzene)-resin

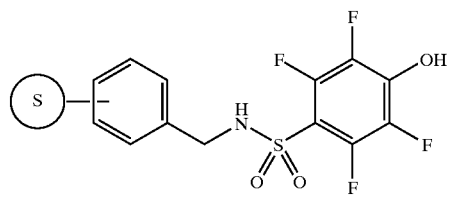

The title resin is prepared according to the method of Example 3, except that 2,3,4,5,6-pentafluorophenylsulfonamidomethyl-copoly(styrene-1%-divinylbenzene)-resin, prepared as in Example 6, is substituted for 2,3,4,5,6-pentafluorobenzoyl-copoly(styrene-1%-divinylbenzene)resin.

EXAMPLE 8

4-Carboxy-2,3,5,6-tetrafluorophenoxymethyl-copoly(styrene-1%-divinylbenzene)resin

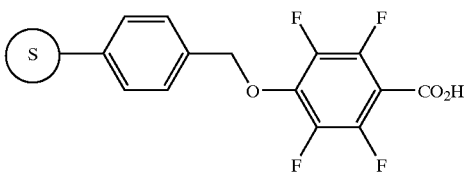

Merrifield resin (2 mmol/g, 600 mg, 1.2 mmol) is swelled in anhydrous DMF (20 mL). 2,3,5,6-tetrafluoro-4-hydroxy benzoic acid hydrate (2.28 g, 10 mmol) and cesium carbonate (3.26 g, 10 mmol) are added, and the reaction mixture is heated at 85° C. for 12 hours with gentle agitation. The reaction mixture is filtered, and the 4-carboxy-2,3,5,6-tetrafluorophenoxymethyl-copoly(styrene-1% divinylbenzene) resin is washed with DMF (5×), 20% aqueous DMF (5×), THF (5×) and dichloromethane and dried overnight in vacuo. IR (microscope, cm–1): 1640 (C=O); $^{19}$F NMR (nanoprobe) –144.4 ppm, –160.2 ppm.

EXAMPLE 9

Determination of Loading of Aminomethyl Resin with 2,3,5,6-Tetrafluoro-4-hydroxybenzoic Acid (TFP) Using $^{19}$F NMR

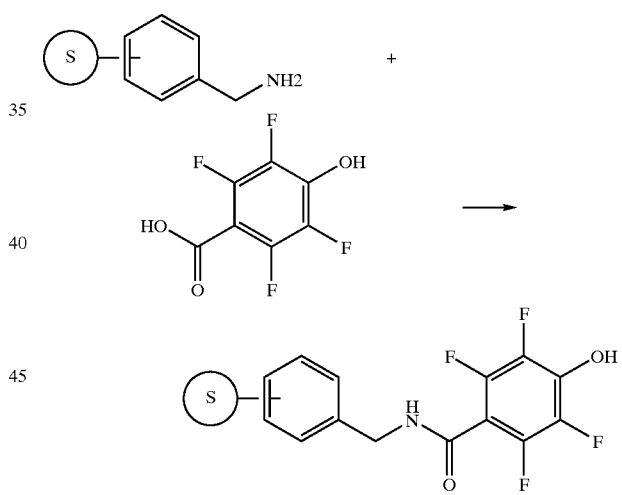

The loading of aminomethyl resin with 2,3,5,6-tetrafluoro-4-hydroxybenzoic acid to produce 4-hydroxy-2,3,5,6-tetrafluorobenzamidomethyl-copoly(styrene-1%-divinylbenzene)-resin is determined by obtaining the $^{19}$F NMR spectrum of a sample consisting of a mixture of 3-fluorobenzamide and 4-hydroxy-2,3,5,6-tetrafluorobenzamidomethyl-copoly(styrene-1%-divinylbenzene)-resin. The integrals of the $^{19}$F resonances corresponding to 3-fluorobenzamide and 4-hydroxy-2,3,5,6-tetrafluorobenzamidomethyl-copoly(styrene-1%-divinylbenzene)-resin are measured and the loading of the resin is then calculated by using formula 1.

The $^{19}$F NMR spectrum is acquired at ambient temperature on a Varian UnityPlus spectrometer operating at 470.23 MHz. The spectrometer is equipped with a single coil proton Nanoprobe tuned to 19F. The sample is prepared by accurately weighing 2–4 mg of resin in a sample tube. To the weighed resin is added microliters of a 0.125 M solution of 3-fluorobenzamide in D$_7$-DMF (Cambridge Isotopes), followed by sufficient D$_7$-DMF to fill the sample tube (total solvent volume is approximately 40 microliters).

The loading of 4 samples of 4-hydroxy-2,3,5,6-tetrafluorobenzamidomethyl-copoly(styrene-1%-divinylbenzene)-resin, prepared using the coupling conditions summarized below, as determined both by $^{19}$F NMR and by combustion analysis, is summarized in Table 1. As shown in Table 1, there is excellent agreement between the resin loading determined by $^{19}$F NMR and the resin loading as determined by combustion analysis.

TABLE 1

Determination of Loading of Aminomethyl Resin with 2,3,5,6-tetrafluoro-4-hydroxybenzoic acid (TFP) using $^{19}$F NMR.

| Sample | Coupling conditions | Resin Loading (mmol TFP/g resin) | |
|---|---|---|---|
| | | $^{19}$F NMR | Combustion analysis |
| 1 | Initial aminomethyl resin loading 0.82 mmol/g. (as in Example 1) | 0.83 | 0.87 |
| 2 | As in Example 1 except initial aminomethyl resin loading 0.39 mmol/g. | 0.27 | 0.28 |
| 3 | As in Example 1, except initial aminomethyl resin loading 0.47 mmol/g. | 0.35 | 0.35 |
| 4 | As in Example 1, except 20% HCl in DMF used instead of 2N HCl/DMF; initial aminomethyl resin loading 0.47 mmol/g. | 0.35 | 0.38 |

EXAMPLE 10

General Procedure for Preparing 2,3,5,6-Tetrafluorobenzamidomethyl-copoly(styrene-1%-divinylbenzene) Activated Ester Resin Compounds

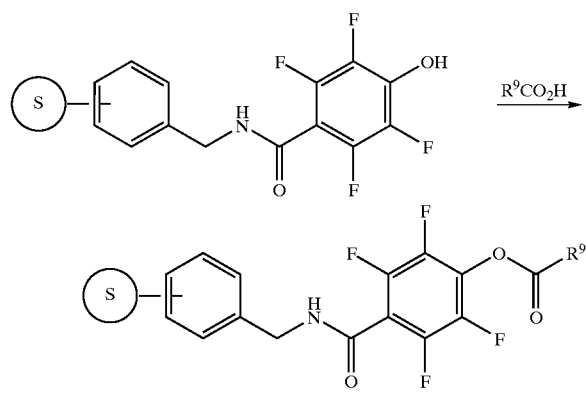

4-Hydroxy-2,3,5,6-tetrafluorobenzamidomethyl-copoly (styrene-1%-divinylbenzene)-resin (0.47 mmol/g, 0.5 g) is weighed into each of forty mL Jones tubes arranged in a test tube rack and DMF (4 mL), diisopropylcarbodiimide (DIC; 0.186 mL, 5 equiv.) and 4-dimethylaminopryidine (DMAP; 43 mg, 1.5 equiv. (1 mL of a stock solution prepared by dissolving 1720 mg of DMAP in 40 mL of DMF)) are added to each tube. The carboxylic acid to be coupled (5 equiv.) is added and the test tube rack is shaken overnight at ambient temperature. The test tube rack is removed from the shaker the resin samples are filtered in two batches of 20. The resin samples are washed with DMF (5×5 ml), THF (5×5 ml) and CH$_2$Cl$_2$ (5×5 ml) and dried overnight at 35° C.

EXAMPLE 11

Monitoring of 4-[1-(4-Trifluoromethylphenyl)-2,5-dimethylpyrrol-4-oyl]oxy-2,3,5,6-tetrafluorobenzamidomethyl-copoly(styrene-1%-divinylbenzene) Formation Using $^{19}$F NMR

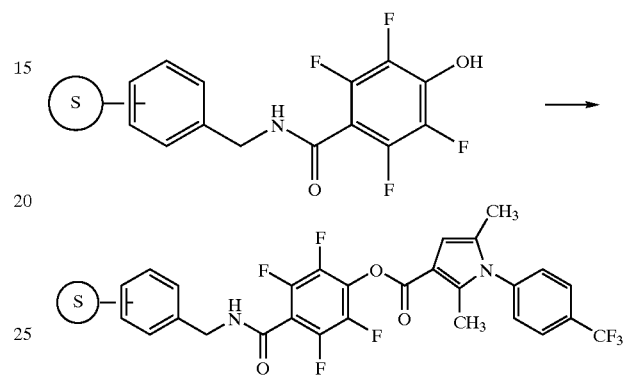

Figure 6:
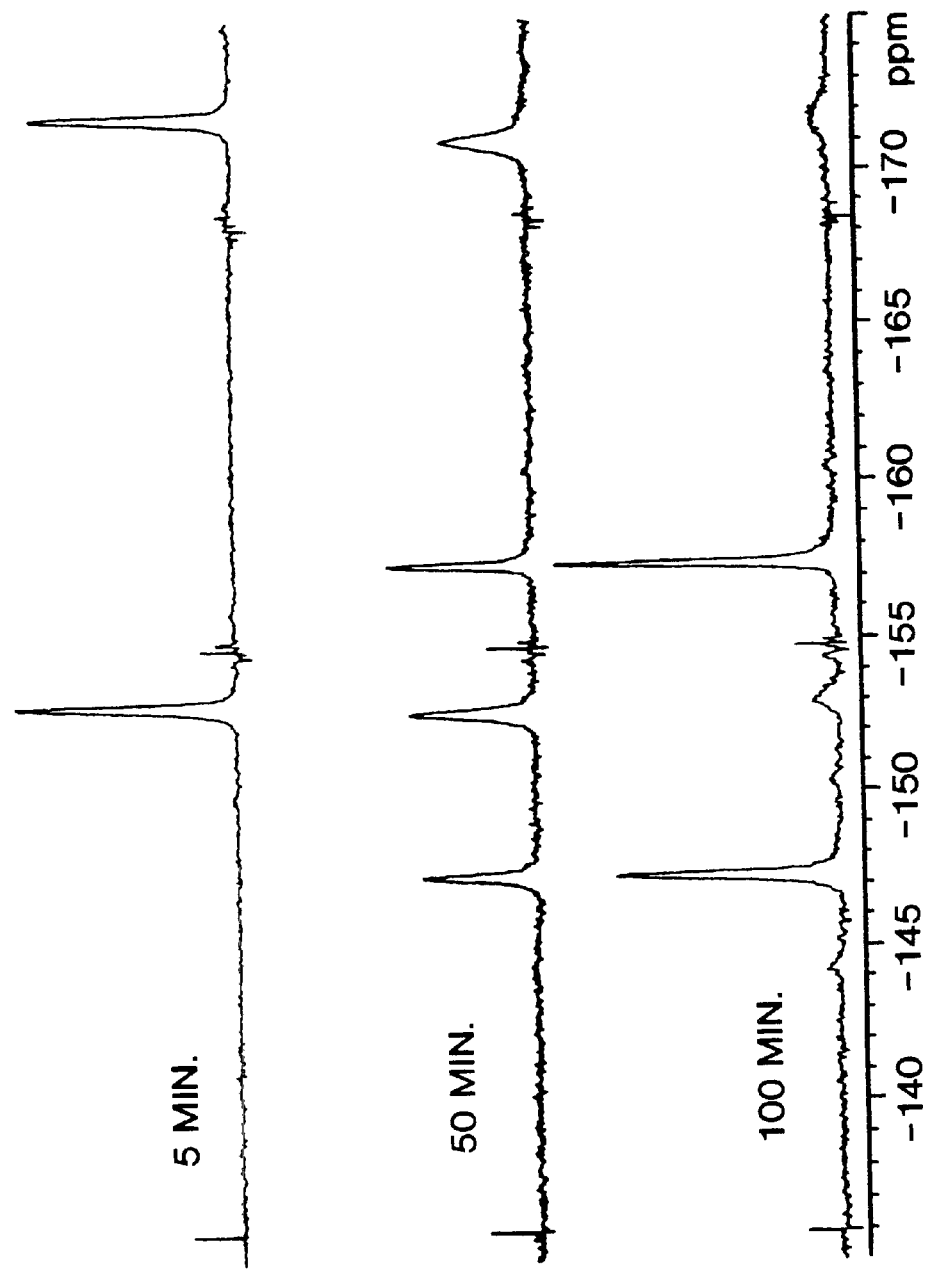
FIG. 6 is the $^{19}$F MAS NMR spectra of a reaction mixture consisting of 4-hydroxy-2,3,5,6-tetrafluorobenzamidomethyl-copoly(styrene-1%-divinylbenzene)-resin, 1-(4-trifluoromethylphenyl)-2,5-pyrrole-4-carboxylic acid (5 equiv.), 4-dimethylaminopyridine (1.5 equiv.) and diisopropylcarbodiimide (5 equiv.) taken at 5 minutes, 50 minutes and 100 minutes. The spectrum at 5 minutes shows $^{19}$F resonances at about −153 and −172 ppm corresponding to the $^{19}$F resonances of 4-hydroxy-2,3,5,6-tetrafluorobenzamidomethyl-copoly(styrene-1%-divinylbenzene)-resin. At 50 minutes, $^{19}$F resonances at about −153 and about −172 ppm corresponding to 4-hydroxy-2,3,5,6-tetrafluorobenzamidomethyl-copoly(styrene-1%-divinylbenzene)-resin, and at about −147 and −158 ppm corresponding to 4-[1-(4-trifluoromethylphenyl)-2,5-dimethylpyrrol-4-oyl]oxy-2,3,5,6-tetrafluorobenzamidomethylcopoly(styrene-1%-divinylbenzene) are present. The spectrum at 100 minutes consists predominately of $^{19}$F resonances at −147 and −158 ppm indicating that that substantially all of the starting 4-hydroxy-2,3,5,6-tetrafluorobenzamidomethyl-copoly (styrene-1%-divinylbenzene)-resin has been converted to product to 4-[1-(4-trifluoromethylphenyl)-2,5-dimethylpyrrol-4-oyl]oxy-2,3,5,6-tetrafluorobenzamidomethyl-copoly(styrene-1%-divinylbenzene)-resin.

The coupling of 4-hydroxy-2,3,5,6-tetrafluorobenzamidomethyl-copoly(styrene-1%-divinylbenzene)-resin and 1-(4-trifluoromethylphenyl)-2,5-dimethyl pyrrole-4-carboxylic acid, using the procedure of Example 10, is monitored using $^{19}$F NMR by removing aliquots of the reaction at selected time periods and obtaining the 19F NMR spectra of the aliquots. As the reaction proceeds, the 19F resonances corresponding to the starting of 4-hydroxy-2,3,5,6-tetrafluorobenzamidomethyl-copoly (styrene-1%-divinylbenzene)-resin are replaced by the 19F resonances corresponding to the product 4-[1-(4-trifluoromethylphenyl)-2,5-dimethylpyrrol-4-oyl]oxy-2,3,5, 6-tetrafluorobenzamidomethyl-copoly(styrene-1%-divinylbenzene) resin. The 19F NMR spectra obtained at 5, 50 and 100 minutes are reproduced in FIG. 6. As shown in FIG. 6, the reaction mixture consists of entirely starting resin at 5 minutes; about equal amounts of starting resin and activated ester resin product at 50 minutes; and almost entirely activated ester resin product at 100 minutes. Exact quantification of the progress of the reaction at a given time period is obtained by integrating the starting resin and product activated ester resin 19F resonances.

EXAMPLE 12

General Procedure for Cleaving 2,3,5,6-Tetrafluorobenzamidomethyl-copoly(styrene-1%-divinylbenzene) Activated Ester Resin Compounds with Amines

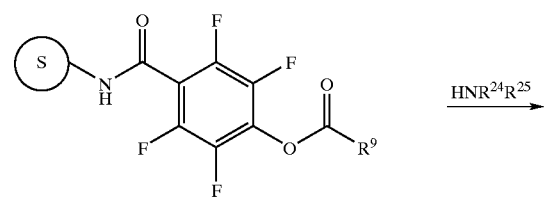

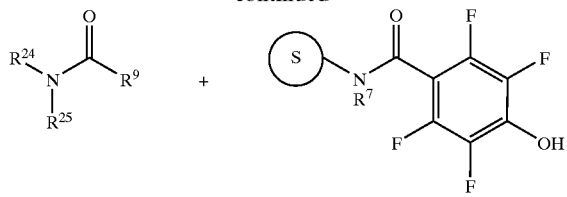

The requisite amount of 2,3,5,6-tetrafluorobenzamidomethyl-copoly(styrene-1%-divinylbenzene) activated ester resin compounds are placed in the desired receptacle i.e. 96 well plates; reaction flasks; test-tubes, etc.

A stock solution of the desired amine in DMF is prepared in a selected container. By any suitable means, i.e. by pipette, or robotic instrument, an amount of the amine stock solution is transferred to each of the resin reaction vessels. The amount of amine transferred is usually 0.8 equivalents of the resin (in mmoles). The reaction vessels are then agitated for about 3 days. The mixture in the reaction vessels is then removed by pipetting or by robotic instruments and filtered through any suitable device, such as Jones filtration tubes or through a Polyfiltronics filtration plate. These procedures allow the free resin to be retained in the filtration device, while the reaction liquid to pass into a collection vessel, such as test tube or a 96 well plate. The filtrate is then concentrated to dryness using any suitable device such as a Turbovac; a Savant or a Genevac evaporator. This process will produce the desired compound as an amide in a form suitable for biological assay. In the case of amines that may be N-protected as Boc, etc., or have t-butyl ester groups present, these can be removed by treating the protected amide product with a mixture of trifluoroacetic acid in methylene chloride in the presence of a trace of water.

EXAMPLE 13

Preparation of Copoly(styrene-4-fluorostyrene-4-chloromethylstyrene-1%-divinylbenzene)-resin

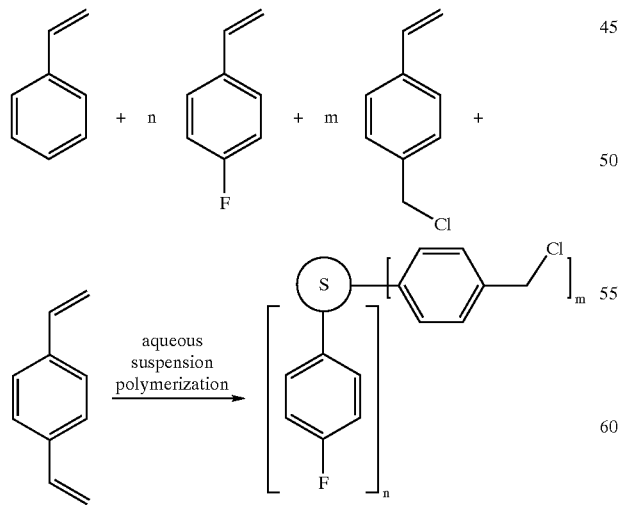

A 1 L cylindrical reaction vessel is charged with 450 mL of deionized water, 4.5 g polyvinylpyrollidone and 0.5 g azoisobutyronitrile. The flask is well purged with nitrogen gas. The mixture is stirred 30 minutes at 200 rpm using a Teflon agitator, then styrene (24 mL), 4-fluorostyrene (11.4 mL), 1,4-divinylbenzene (0.6 mL) and 4-vinylbenzylchloride (13.8 mL) are added. The mixture is next stirred at 305 rpm at room temperature for 1 hour, then heated to 80° C. for 18 hours to complete the polymerization reaction. After cooling, the resin is washed with water (1.5 L), methanol (1.0 L) and DMF (2×500 mL) prior to drying in vacuo. Elemental analysis of the copoly(styrene-4-fluorostyrene-4-chloromethylstyrene-1%-divinylbenzene) resin gives 7.41% Cl and 3.22% F. The IR spectrum of the product resin shows 1266 cm$^{-1}$ (—CH$_2$Cl wag) and −1223 cm$^{-1}$ (C—F stretch), and the $^{19}$F NMR shows a single resonance at −121 ppm.

EXAMPLE 14

Preparation of 4-Fluorophenoxymethyl-copoly(styrene-1%-divinylbenzene-4-chloromethylstyrene)-resin by Partial Modification of Merrifield Resin

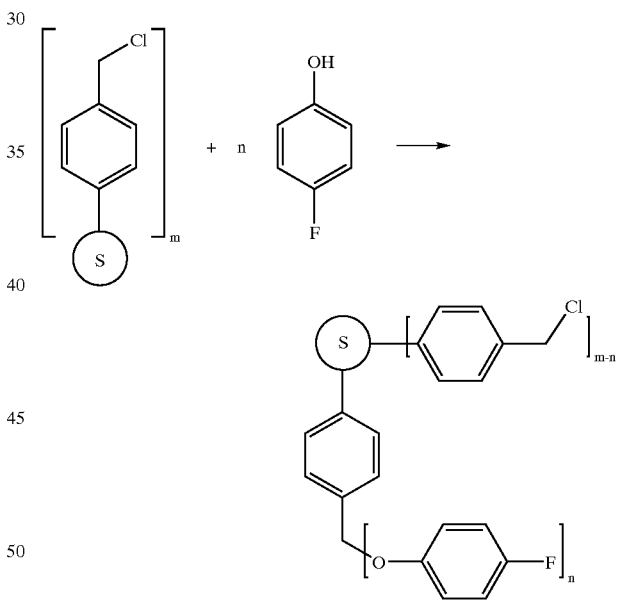

Merrifield resin (2 mmol/g, 1.0 g, 2.0 mmol) is swelled in anhydrous N,N-dimethylformamide (DMF) (25 mL). A solution of 4-fluorophenol (0.7 mmol, 78 mg) and sodium hydroxide (0.75 mmol, 0.75 mL of 1.0 N aqueous solution) in 3 mL of dimethylsulfoxide is added and the reaction mixture is heated at 80° C. for 30 hours with gentle agitation. After cooling, the resin is washed sequentially with DMF (2×25 mL), 2% aqueous HCl: DMF (1 mL: 4 mL; 2×25 mL), DMF (2×25 mL), and finally CH$_2$Cl$_2$ (2×25 mL). The product is dried in vacuo, then stored at −5° C. until used.

EXAMPLE 15

Preparation of 4-Fluorobenzoatemethyl-copoly(styrene-4-fluorostyrene)-1%-divinylbenzene)-resin

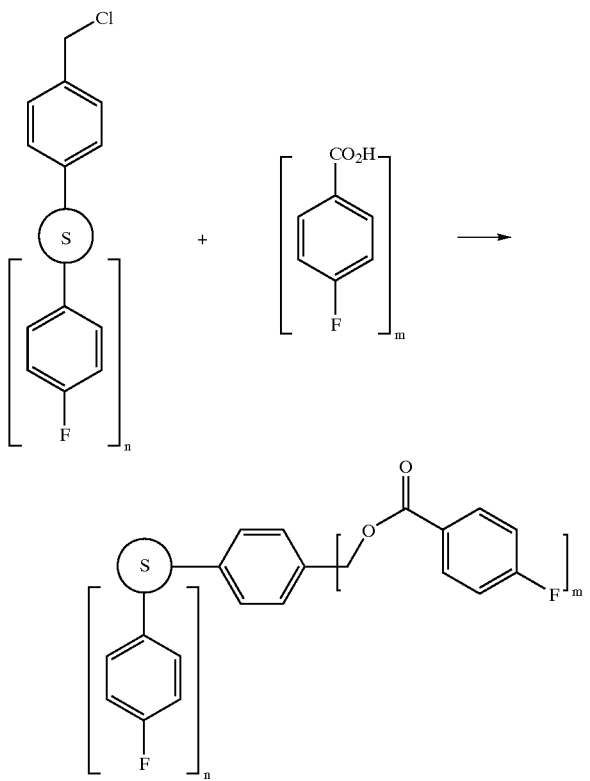

Figure 8:
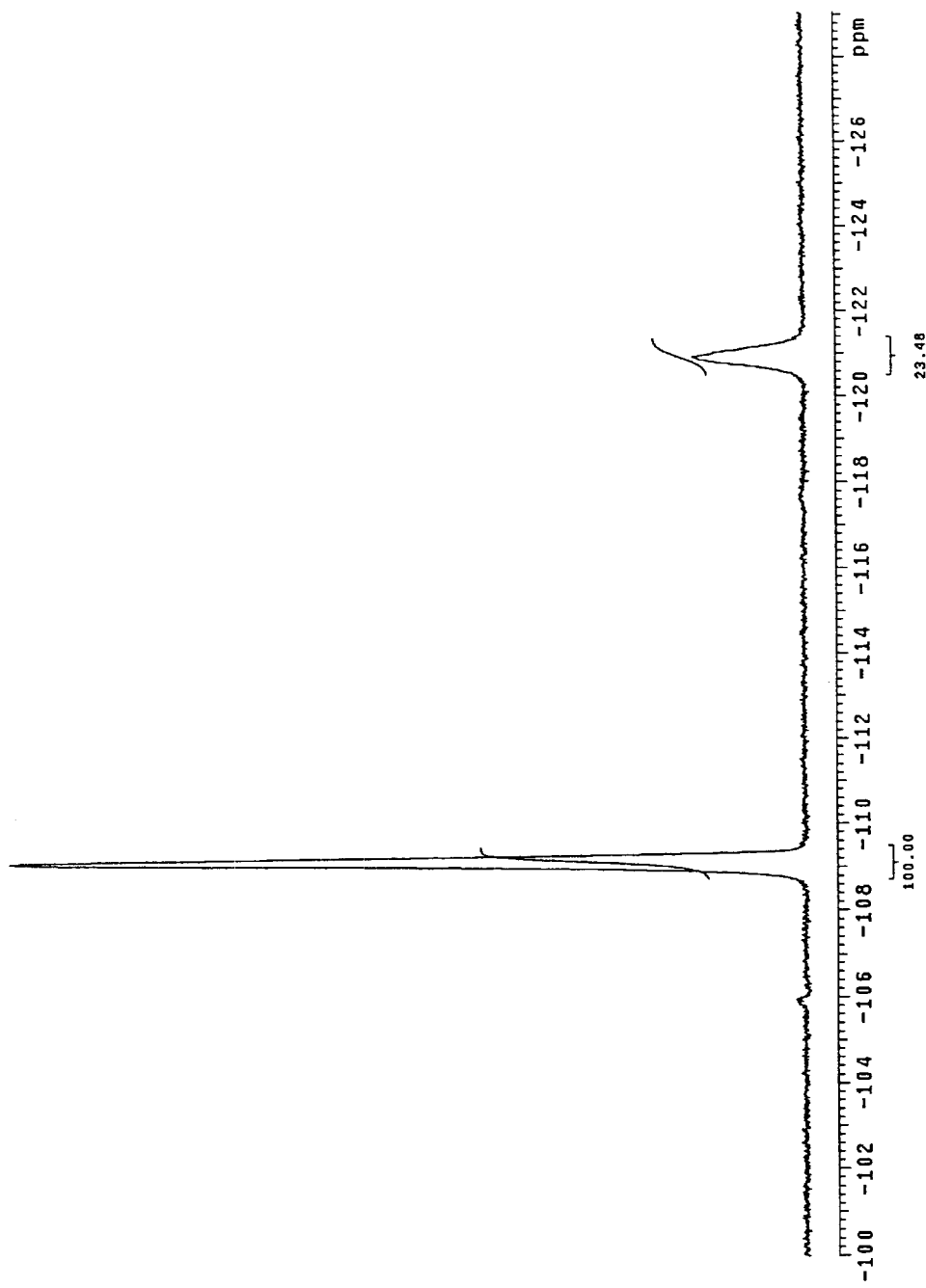
FIG. 8 is the $^{19}$F MAS NMR spectrum of copoly(styrene-4-fluorostyrene-4-chloromethylstyrene-1%-divinylbenzene)-resin after reaction with 4-fluorobenzoic acid in the presence of CsCO$_3$ in N,N-dimethylformamide at 80° C. The $^{19}$F resonances at approximately −121 and −109 ppm correspond to, respectively, the internal standard (0.40 mmol/g) and the appended 4-fluorobenzoate ester (1.70 mmol/g).

The title resin is prepared by reacting a mixture of copoly(styrene-4-fluorostyrene-4-chloromethylstyrene-1%-divinylbenzene)-resin (100.0 mg; 0.16 mmol), 4-fluorobenzoic acid (0.110 g; 0.8 mmol; 5 eq.), and cesium carbonate (0.52g; 1.6 mmol; 10 eq) in 4 mL of anhydrous DMF with stirring at 80° C. for approximately 12 hours. After cooling and filtering, the resin was washed in turn with DMF (3×5 mL), DMF: 1N HCl (3:1; 3×5 mL), THF:H(3:1; 3×5 mL) and TRF (3×5 then dried in vacuo at 40° C. The $^{19}$F NMR spectrum of the product resin is shown in FIG. 8. The product resin 4-fluorobenzoate loading is 1.70 mmol/g as determined by calculation according to formula 1 (vide supra) using the $^{19}$F NMR integral values.

EXAMPLE 16

Preparation of 4-(1-Ethanone)-2-(fluorophenoxymethyl)-copoly (styrene-1% divinylbenzene)resin

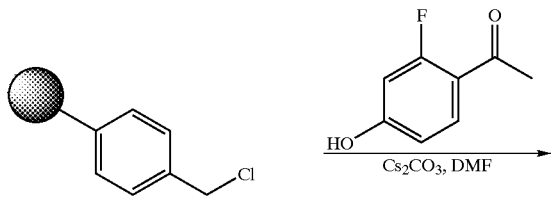

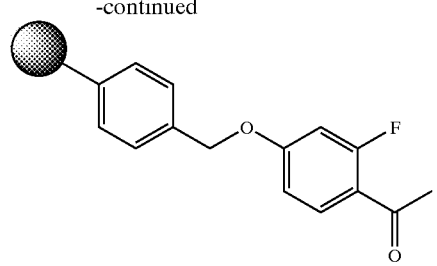

-continued

To a suspension of chloromethyl polystyrene (Merrifield resin) (5.0 g, 8.9 mmol, resin loading 1.78 mmol/g) and cesium carbonate (29.0 g, 90 mmol, 10 eq.) in dry DMF (100 ml) was added 4-hydroxy-2-fluoroacetophenone (6.9 g, 45 mmol, 5 eq.) in dry DMF (20 ml). The mixture was mechanically stirred at 80° C. for 24 hours. The solution was cooled, washed with THF: 1N HCl soln. (3:1, ×3), THF:H$_2$O (3:1, ×3), THF (×3) and DCM (×3). The 4-(1-ethanone)-2-fluorophenoxymethyl)-copoly (styrene-1% divinylbenzene) resin was dried in vacuo at 40° C. overnight. IR (C=O) 1682 cm$^{-1}$. d$^{19}$F (CDCl$_3$) −108 ppm. Theoretical loading 1.47 mmol/g. Analysis found C, 80.04; H, 6.47; F, 2.92, which corresponds to 1.53 fluorine atoms/g; 1.47 calculated for 100% loading.

EXAMPLE 17

Preparation of 4-(Hydroxylethyl)-2-(fluorophenoxymethyl)-copoly(styrene-1% divinylbenzene)resin

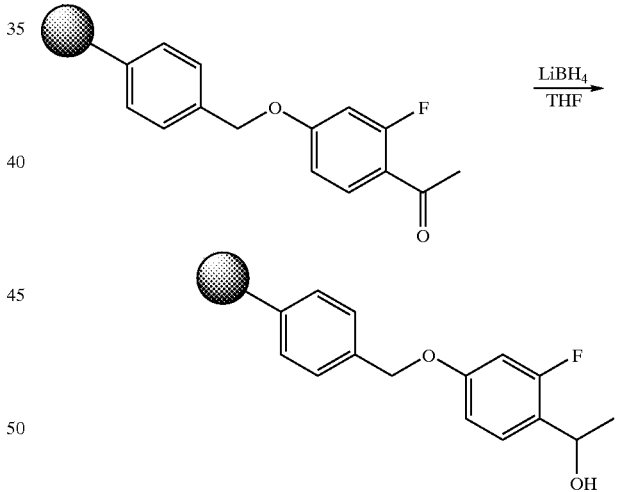

To a suspension of the 4-(1-ethanone)-2-fluorophenoxymethyl)-copoly(styrene-1% divinylbenzene) resin (0.25 g, 0.37 mmol) in dry THF was added lithium borohydride (0.93 ml of a 2.0 M soln. in THF, 1.85 mmol, 5 eq.). The mixture was shaken at room temperature for 4 hours. The resin was filtered, washed with THF (×3), THF:H$_2$O (3:1, ×3), THF (×3) and DCM (×3). The 4-(hydroxylethyl)-2-fluorophenoxymethyl)-copoly (styrene-1% divinylbenzene) resin was dried in vacuo at 40° C. overnight. IR (C=O) disappears. d$^{19}$F (CDCl$_3$) −121 ppm. Theoretical loading 1.47 mmol/g. Analysis found C, 78.02; H, 6.79; F, 2.76, which corresponds to 1.45 fluorine atoms/g; 1.47 calculated for 100% loading.

What is claimed is:

1. A method of quantitating a solid-phase reaction comprising:

(a) initiating a solid-phase reaction between a fluorine-containing solid-phase reaction component comprising a fluorine-containing support with fluorine atom(s) as an internal standard, and a reactant or fluorine-containing reactant to form a fluorine-containing solid-phase reaction product;

(b) taking a sample of said solid-phase reaction at a predetermined time interval and obtaining a $^{19}F$ NMR spectrum of said sample; and (c) comparing, in said $^{19}F$ NMR spectrum, the intensity or integral corresponding to the fluorine-containing solid-phase reaction product $^{19}F$ resonance to the intensity or integral corresponding to $^{19}F$ resonance of said internal standard.

2. The method according to claim 1 wherein said $^{19}F$ NMR spectrum is obtained using any $^{19}F$ NMR technique including magic angle spinning.

3. The method according to claim 1 wherein the fluorine-containing solid-phase reaction component is of formula

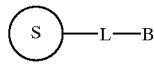

wherein

is a solid fluorine-containing support;

L is a chemical bond or a linking group optionally containing one or more fluorine atoms, provided that at least one of the solid support and the linking group contains at least one fluorine atom; and B is a functional group suitable for reaction with a reactant or fluorine-containing reactant to form a fluorine-containing solid-phase product.

4. The method according to claim 3 wherein the solid support contains one or more fluorine atoms.

5. The method according to claim 3 wherein

is a solid support;

L is a group of formula

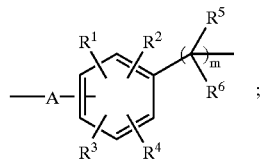

A is a chemical bond or is selected from

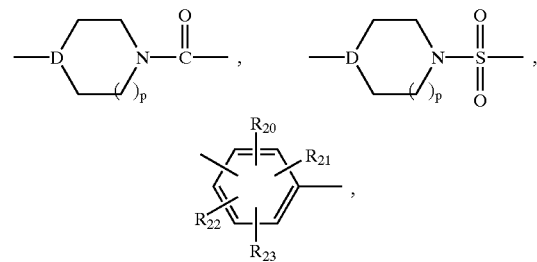

—C(O)—, —YC(O)—, —SO$_2$—, —NR$^7$SO$_2$—, —CHR$^7$—, —CHR$^7$Y— and —CHR$^7$YC(O)(CH$_2$)$_m$— or when B is halogen, NHP, OW or SO$_2$Z;

D is CH or N;

P is H or an amine protecting group;

W is H, NHP, NPR$^9$, —NR$^{10}$C(O)Cl, C(O)R$^9$, C(O)NR$^{10}$R$^{11}$, C(O)OR$^9$, SO$_2$R$^9$ or C(O)-imidazol-1-yl;

Y is —O— or —NR$^8$—;

Z is Cl, OH, OR$_a$ or NR$^9$R$^{12}$;

R$^1$ is F, or when one of R$^{16}$, R$^{17}$, R$^{18}$ and R$^{19}$ is F, R$^1$ is H, alkyl, alkoxy, halogen, CN or NO$_2$;

R$^2$, R$^3$ and R$^4$ are independently H, alkyl, alkoxy, halogen, CN or NO$_2$, or one of R$^1$, R$^2$ and R$^4$, taken together with one of R$^5$ and R$^6$ and the carbon atoms to which they are attached, define a group of formula

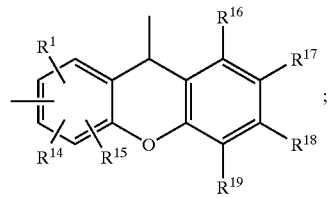

R$^5$ and R$^6$ are independently —H, alkyl, phenyl or phenyl substituted with one or more substituents selected from alkyl, alkoxy, halogen, nitrile and —NO$_2$;

R$^7$ and R$^8$ are independently H or lower alkyl;

R$^9$ and R$^{13}$ are independently aliphatic or aromatic;

R$^{10}$ and R$^{11}$ are independently H, aliphatic or aromatic;

R$^{12}$ is —CH$_2$R$^{13}$;

R$^{14}$, R$^{15}$, R$^{16}$, R$^{17}$, R$^{18}$, R$^{19}$, R$^{20}$, R$^{21}$, R$^{22}$ and R$^{23}$ are independently selected from H, alkyl, alkoxy, halogen, —CN and —NO$_2$;

m is 0 or 1;

n is 1–6; and p is 0, 1 or 2.

6. The method according to claim 5 wherein R$^1$, R$^2$, R$^3$ and R$^4$ are F; and one of R$^5$ and R$^6$ is H and the other of R$^5$ and R$^6$ is H or 2,4-dimethoxyphenyl.

7. The method according to claim 6 wherein B is F, OW or SO$_2$Z.

8. The method according to claim 7 wherein A is phenylene, —C(O)—, —YC(O)—, —SO$_2$—, —NR$^7$SO$_2$— or —CHR$^7$O—.

9. The method according to claim 5 wherein the fluorine-containing solid-phase reaction component is selected from 4-carboxy-2,3,5,6-tetrafluorophenoxymethyl-copoly(styrene-1% divinylbenzene) resin, 4-(O-methylhydroxylamine)-2,3,5,6-tetrafluorophenoxymethyl-copoly(styrene-1% divinylbenzene) resin, 4-(2',4'-dimethoxyphenyl-O-methylhydroxylamine)-2,3,5,6-tetrafluorophenoxymethyl-copoly(styrene-1% divinylbenzene) resin, 4-hydroxy-2,3,5,6-tetrafluorobenzamidomethyl-polystyrene resin, 2,3,5,6-tetrafluorobenzamidomethyl-4-sulfonic acid-polystyrene resin, 2,3,5,6-tetrafluorobenzamidomethyl-4-sulfonyl chloride-polystyrene resin, 4-hydroxy-2,3,5,6-tetrafluorobenzoyloxymethyl-polystyrene resin, 2,3,5,6-tetrafluorobenzoyloxymethyl-4-sulfonic acid-polystyrene resin, 2,3,5,6-tetrafluorobenzoyloxymethyl-4-sulfonyl chloride-polystyrene resin, 4-hydroxy-2,3,5,6-pentafluorobenzoyl-polystyrene resin, 2,3,5,6-tetrafluorobenzoyl-4-sulfonic acid-polystyrene resin, 2,3,5,6-tetrafluorobenzoyl-4-sulfonyl chloride-polystyrene resin, 4-hydroxy-2,3,5,6-tetrafluorophenylsulfonamidomethyl-polystyrene resin, 2,3,5,6-tetrafluorophenyzsulfonamidomethyl-4-sulfonic acid-polystyrene resin, 2,3,5,6-tetrafluorophenyzsulfonamidomethyl-4-sulfonyl chloride-polystyrene resin, N-(4-hydroxy-2,3,5,6-tetrafluorobenzoyl)-piperidinomethyl-polystyrene resin, N-(2,3,5,6-tetrafluorobenzoyl-4-sulfonic acid)-piperidinomethyl-polystyrene resin, N-(2,3,5,6-tetrafluorobenzoyl-4-sulfonyl chloride)-piperidinomethyl-4-polystyrene resin, N-(4-hydroxy-2,3,5,6-tetrafluorophenyzsulfonyl)-piperidinomethyl-polystyrene resin, N-((2,3,5,6-tetrafluorophenyl-4-sulfonic acid)sulfonyl)-piperidinomethyl-polystyrene resin, N-((2,3,5,6-tetrafluorophenyl-4-sulfonyl chloride)sulfonyl)-piperidinomethyl-polystyrene resin, 4-hydroxy-2,3,5,6-tetrafluorophenyl-polystyrene resin, 2,3,5,6-tetrafluorophenyl-4-sulfonic acid-polystyrene resin, 2,3,5,6-tetrafluorophenyl-4-sulfonyl chloride polystyrene resin, 4-hydroxy-2,3,5,6-tetrafluorophenylsulfonyl-polystyrene resin, 2,3,5,6-tetrafluorophenylsulfonyl-4-sulfonic acid-polystyrene resin, and 2,3,5,6-tetrafluorophenylsulfonyl-4-sulfonyl chloride-polystyrene resin.

10. The method according to claim 5 wherein the fluorine-containing solid-phase reaction component is selected from 4-carboxy-2,3,5,6-tetrafluorophenoxymethyl-copoly(styrene-1% divinylbenzene) resin, 4-(O-methylhydroxylamine)-2,3,5,6-tetrafluorophenoxymethyl-copoly(styrene-1% divinylbenzene) resin, 4-(2',4'-dimethoxyphenyl-O-methylhydroxylamine)-2,3,5,6-tetrafluorophenoxymethyl-copoly(styrene-1% divinylbenzene) resin, 4-hydroxy-2,3,5,6-tetrafluorobenzamidomethyl-polystyrene resin, 2,3,5,6-tetrafluorobenzamidomethyl-4-sulfonic acid-polystyrene resin, designated herein as 2,3,5,6-tetrafluorobenzamidomethyl-4-sulfonyl chloride-polystyrene resin, 4-hydroxy-2,3,5,6-pentafluorobenzoyl-polystyrene resin, 2,3,5,6-tetrafluorobenzoyl-4-sulfonic acid-polystyrene resin, 2,3,5,6-tetrafluorobenzoyl-4-sulfonyl chloride-polystyrene resin, 4-hydroxy-2,3,5,6-tetrafluorophenylsulfonamidomethyl-polystyrene resin, 2,3,5,6-tetrafluorophenylsulfonamidomethyl-4-sulfonic acid-polystyrene resin and 2,3,5,6-tetrafluorophenylsulfonamidomethyl-4-sulfonyl chloride-polystyrene resin.

11. The method according to claim 5 wherein the fluorine-containing solid-phase reaction component is 4-hydroxy-2,3,5,6-tetrafluorobenzamidomethyl-polystyrene resin.

* * * * *